United States Patent
Kwon et al.

(10) Patent No.: US 11,618,916 B2
(45) Date of Patent: Apr. 4, 2023

(54) PROBE FOR MEASURING ACTIVITY OF CASPASE-1 AND COMPOSITION FOR DIAGNOSIS OF INFLAMMATORY DISEASES CONTAINING SAME

(71) Applicants: KOREA INSTITUTE OF SCIENCE AND TECHNOLOGY, Seoul (KR); SEOUL NATIONAL UNIVERSITY R&DB FOUNDATION, Seoul (KR)

(72) Inventors: Ick Chan Kwon, Seoul (KR); Ju Hee Ryu, Seoul (KR); Young-Ji Ko, Seoul (KR); Hye-Sun Kim, Seoul (KR); Nam-Hyuk Cho, Seoul (KR); Eun-Jeong Yang, Seoul (KR); Jae Won Lee, Daegu (KR)

(73) Assignees: Korea Institute of Science and Technology, Seoul (KR); Seoul National University R&DB Foundation, Seoul (KR)

( * ) Notice: Subject to any disclaimer, the term of this patent is extended or adjusted under 35 U.S.C. 154(b) by 305 days.

(21) Appl. No.: 16/568,363

(22) Filed: Sep. 12, 2019

(65) Prior Publication Data
US 2020/0087705 A1 Mar. 19, 2020

(30) Foreign Application Priority Data
Sep. 13, 2018 (KR) .................... 10-2018-0109757

(51) Int. Cl.
*C12Q 1/37* (2006.01)
*G01N 33/573* (2006.01)

(52) U.S. Cl.
CPC ............. *C12Q 1/37* (2013.01); *G01N 33/573* (2013.01); *G01N 2333/96466* (2013.01)

(58) Field of Classification Search
None
See application file for complete search history.

(56) References Cited

FOREIGN PATENT DOCUMENTS

| KR | 10-1103548 B1 | 1/2012 |
| KR | 10-2016-0095187 A | 8/2016 |

OTHER PUBLICATIONS

Liu et al, Single-Cell Imaging of Caspase-1 Dynamics Reveals an All-or-None Inflammasome Signaling Response. Cell Reports 8, 974-982, Aug. 21, 2014.*
Messerli et al, A Novel Method for Imaging Apoptosis Using a Caspase-1 Near-Infrared Fluorescent Probe. Neoplasia. Mar. 2004; 6(2): 95-105.*
Anani et al, Nanoparticle-based probes to enable noninvasive imaging of proteolytic activity for cancer diagnosis. Nanomedicine (Lond.) (2016) 11(15), 2007-2022.*
Shanta M. Messerli et al., "A Novel Method for Imaging Apoptosis Using a Caspase-1 Near-Infrared Fluorescent Probe", Neoplasia, Mar./Apr. 2004, pp. 95-105, vol. 6, No. 2.

* cited by examiner

*Primary Examiner* — Tekchand Saidha
(74) *Attorney, Agent, or Firm* — Rabin & Berdo, P.C.

(57) ABSTRACT

A probe for measuring the activity of caspase-1 according to the present disclosure can specifically image cells or tissues where inflammatory response is induced because it is cleaved by reacting specifically with the active caspase-1 enzyme in vivo and in vitro and re-emits fluorescence. The probe for measuring the activity of caspase-1 can be used for various purposes, such as for imaging of cells or tissues where inflammatory response is induced, as a drug carrier, for screening of a drug inhibiting inflammatory response, etc.

The probe for measuring the activity of caspase-1 is applicable both in vivo and in vitro, and can be used for various applications such as high-throughput screening for new drug development, early diagnosis of diseases, etc.

6 Claims, 19 Drawing Sheets

Specification includes a Sequence Listing.

*P<0.05, **P<0.01, one-way ANOVA and Bonferroni Test

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Trp Glu His Asp Gly Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Leu Glu His Asp Gly Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: SIRPa
      recombinant protein

<400> SEQUENCE: 3

Gly Tyr Val Ala Asp Gly Lys
1               5
```

PROBE FOR MEASURING ACTIVITY OF CASPASE-1 AND COMPOSITION FOR DIAGNOSIS OF INFLAMMATORY DISEASES CONTAINING SAME

CROSS-REFERENCE TO RELATED APPLICATIONS

This application claims, under 35 U.S.C. § 119, the priority of Korean Patent Application No. 10-2018-0109757 filed on Sep. 13, 2018 in the Korean Intellectual Property Office, the disclosure of which is incorporated herein by reference in its entirety.

SEQUENCE LISTING

This application contains a Sequence Listing submitted via EFS-Web and hereby incorporated by reference in its entirety. The Sequence Listing is named SEQCRF-CHIP-157-KIST.txt, created on May 12, 2021, and 994 bytes in size.

TECHNICAL FIELD

The present disclosure relates to a probe capable of measuring the activity of caspase-1, more particularly to a probe having a new structure in which a fluorophore and a quencher are bound to a polypeptide cleaved by caspase-1 and exhibiting fluorescence in the presence of caspase-1, and a composition for diagnosing an inflammatory disease, which contains the same.

BACKGROUND

There exist several defense mechanisms that protect our bodies from risks from outside. These defense mechanisms are collectively called 'immunity'. Specifically, a foreign material invading from invading from outside or an internal existing in the body, which causes problems in the body, is called an 'inflammation source'. And, immune cells in the body respond in various ways to remove the inflammation source. This is called immune response. 'Caspase-1' is an inflammatory protease which reacts with the inflammation source and serves as an 'initiator' that transfers the signal to other immune cells.

The caspase-1 enzyme exists at very low levels in the body at normal times. But, when an inflammation source is recognized, it is activated and plays an important role of informing the danger signal. To be specific, an inflammation source invading the body is recognized with specific receptors by immune cells. Then, an 'inflammasome', which is a multiprotein oligomer consisting of procaspase-1, etc., is formed. Although the mechanism of action of the inflammasome is not clearly known, it is known to play a critical role in inflammatory responses. According to the current knowledge, the inflammasome forms active caspase-1 from procaspase-1 through self-cleavage. The formation of the caspase-1 enzyme is an early immune response occurring during the early phase of inflammatory response, i.e., between 1 hour and 12 hours. That is to say, because it occurs in the early stage of inflammation before an inflammatory disease becomes severe, it is expected that it can be used for early diagnosis of inflammations.

However, there remain many problems to quantitatively analyze or image the activity and expression level of the caspase-1 enzyme existing in the body. First, because the caspase-1 enzyme exists in the cytoplasm of cells, it is difficult to detect only with blood. The currently known experimental methods for detection of the caspase-1 enzyme include protein quantification by electrophoresis, enzyme-linked immunosorbent assay (ELISA), etc. However, these methods have the problems that proteins should be extracted from the target site of a subject, an invasive procedure is unavoidable for the extraction of proteins, the extraction procedure is complicated, equipment and experienced experts are necessary for measurement, and time is required until the result is obtained. For these reasons, early diagnosis of diseases is impossible because the caspase-1 enzyme in the body cannot be measured in real time or directly.

Accordingly, in order to solve the problems described above, development of a new technology which allows exact detection and diagnosis of caspase-1 in real time with biocompatibility is necessary.

REFERENCES OF THE RELATED ART

Patent Document (Patent document 1) Patent document 1. Korean Patent Publication No. 10-2016-0095187.

SUMMARY

The present disclosure is directed to providing a probe for measuring the activity of caspase-1, which is capable of emitting fluorescence spontaneously in a cell by being specifically cleaved by the active caspase-1 enzyme, and a composition for qualitative or quantitative analysis of the caspase-1 enzyme, which contains the same as an active ingredient.

The present disclosure is also directed to providing a composition for screening a drug inhibiting the activation of the caspase-1 enzyme, which contains the probe for measuring the activity of caspase-1 as an active ingredient, and an application thereof.

The present disclosure provides a probe for measuring the activity of caspase-1, wherein a fluorophore (b) and a quencher (c) are bound to both ends of a polypeptide (a) consisting of 4-7 amino acid residues and being cleaved specifically by caspase-1.

The polypeptide (a) may be any one selected from amino acid sequences represented by SEQ ID NOS 1-3.

The fluorophore (b) may be bound to the N-terminal of the polypeptide (a), and the quencher (c) may be bound to the ε-amine group of a lysine or arginine amino acid residue of the polypeptide (a).

The probe for measuring the activity of caspase-1 may emit fluorescence by active caspase-1 through an inflammation response.

The fluorophore (b) may be any one selected from a group consisting of fluorescein, fluorescein isothiocyanate (FITC), Oregon green, Texas red, Cy2, Cy3, Cy3B, Cy3.5, Cy5, Cy5.5, Cy7, indocarbocyanine, rhodamine, oxacarbocyanine, thiacarbocyanine, merocyanine, pyrodyloxazole, nitrobenzoxadiazole, benzoxadiazole, Nile red, Nile orange, acridine yellow, aumarine, crystal violet and malachite green.

The quencher (c) may be any one selected from a group consisting of TAMRA (6-carboxytetramethyl-rhodamine), black hole quencher 1 (BHQ1), black hole quencher 2 (BHQ2), black hole quencher 3 (BHQ3), nonfluorescent quencher (NFQ), DABCYL, Eclipse, deep dark quencher (DDQ), BlackBerry Quencher and Iowa black.

The probe for measuring the activity of caspase-1 may be cleaved by the active caspase-1 enzyme expressed specifically in an inflammatory cell, thereby restoring fluorescence.

The probe for measuring the activity of caspase-1 may further contain a drug or a nanoparticle, and the drug or the nanoparticle may be bound to a carboxyl group at the C-terminal of the polypeptide (a).

The probe for measuring the activity of caspase-1 may be for diagnosing one or more disease selected from a group consisting of squamous cell carcinoma, uterine cancer, cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, kidney cancer, bladder cancer, ovarian cancer, bile duct cancer, gallbladder cancer, dementia, stroke, osteoarthritis and rheumatoid arthritis.

The present disclosure also provides a composition for qualitatively or quantitatively analyzing the caspase-1 enzyme expressed in a cell or a tissue, which contains the probe for measuring the activity of caspase-1 as an active ingredient.

The present disclosure also provides a composition for screening a drug inhibiting the activation of the caspase-1 enzyme, which contains the probe for measuring the activity of caspase-1 as an active ingredient.

The present disclosure also provides a method for imaging a cell or a tissue where an inflammatory response is induced from an individual, which includes: 1) a step of administering the probe for measuring the activity of caspase-1 to the individual; and 2) a step of obtaining an image with the probe for measuring the activity of caspase-1 from the individual.

The probe for measuring the activity of caspase-1 according to the present disclosure can effectively diagnose and image a cell where an inflammatory response is induced because it is activated by reacting specifically with the caspase-1 enzyme activated due to the inflammatory response.

In addition, the probe for measuring the activity of caspase-1 can diagnose the inflammatory response accurately and quickly because it infiltrates into a cell effectively and emits fluorescence only in the presence of the active caspase-1 enzyme in the cell, i.e., only in the cell where the inflammation response is induced.

The probe for measuring the activity of caspase-1 according to the present disclosure is advantageous in that the problems of the existing material for analysis of caspase-1, i.e., difficulty in (invasive) sampling, low accuracy of analysis, difficulty in the analysis of caspase-1 beyond the sampling site, etc., can be solved and that the cell in which the active caspase-1 enzyme exists can be imaged without an additional carrier or nanocarrier. In addition, the probe for measuring the activity of caspase-1 has the great advantage that tissues or cells throughout the body where an inflammatory response is induced can be imaged with single administration.

DETAILED DESCRIPTION OF EMBODIMENTS

Figure 1A:
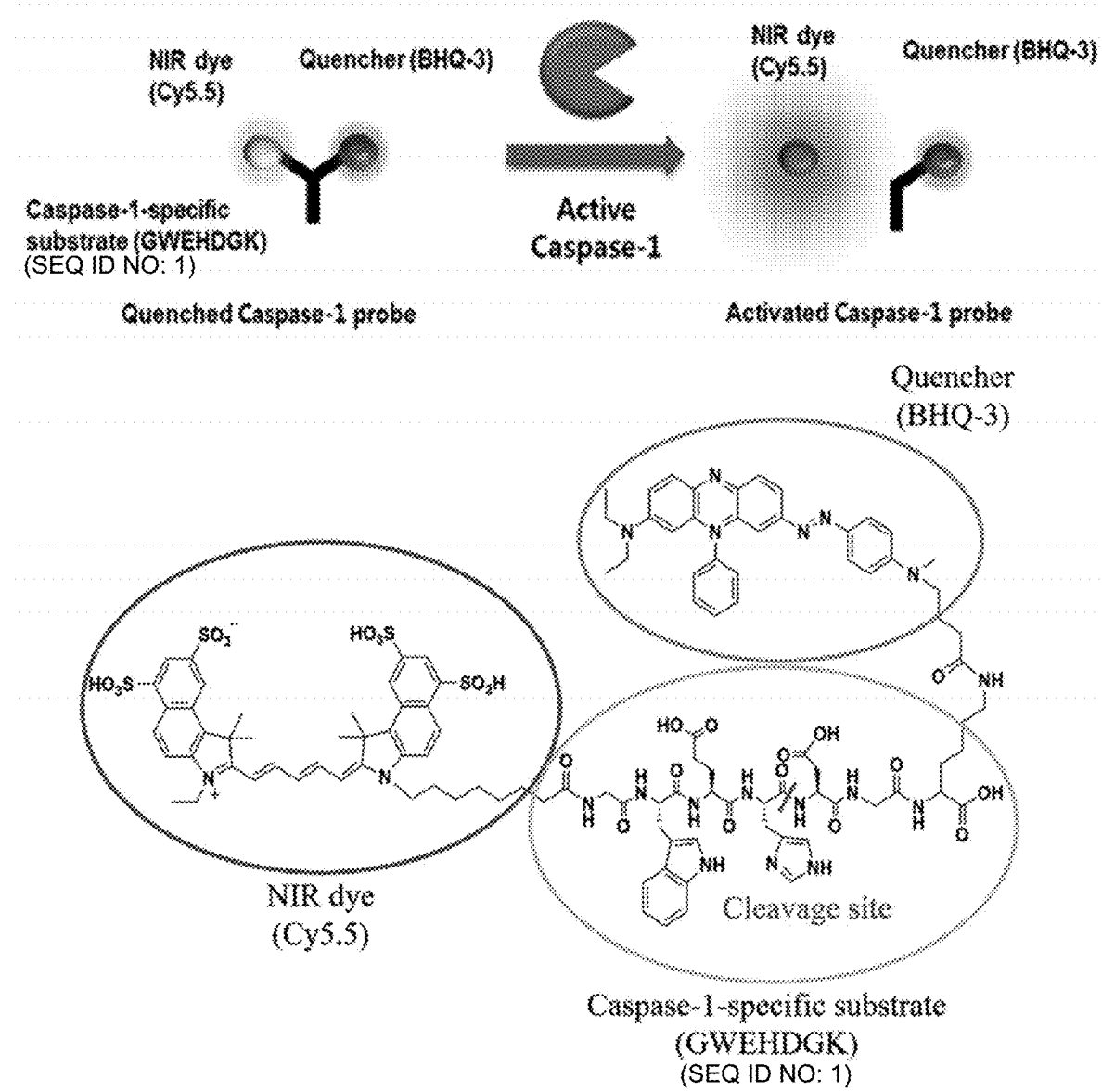
FIG. 1A shows the chemical formula of a probe for measuring the activity of caspase-1, which is cleaved in a cell, and its mechanism of action by the caspase-1 enzyme. It is based on a polypeptide (WEHD (SEQ ID NO: 4)) cleaved by the active caspase-1 enzyme. Glycine (Gly, G) is bound to both ends of the polypeptide. The near-infrared fluorophore Cy5.5 is introduced to a peptide having an amine group (lysine, K), and a quencher (BHQ-3) is bound to the ε-amine group of lysine or arginine located at the N-terminal. Each synthesis procedure is conducted in DMSO in the presence of N-methylmorpholine (NMM) and 4-dimethylaminopyridine (DMAP) catalysts. Each synthesis procedure consists of the three steps of fluorophore introduction, protecting group removal and quencher introduction. In each process, high-performance liquid chromatography (HPLC) is carried out for identification and purification.
Figure 1B:
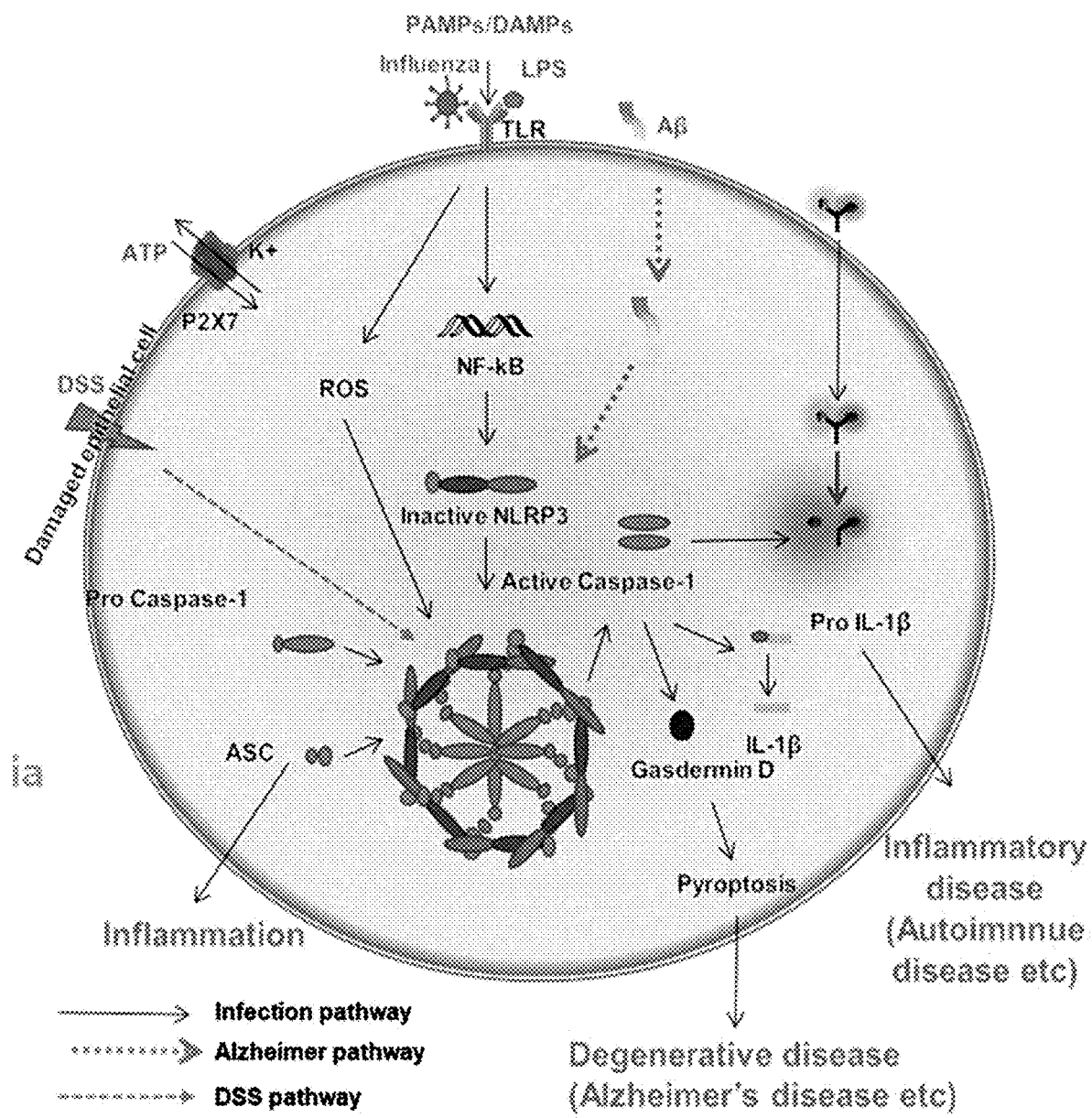
FIG. 1B shows various mechanisms of action of activating the caspase-1 enzyme in a cell, and the mechanism of action of a probe for measuring the activity of caspase-1 of the present disclosure and the caspase-1 enzyme.

Hereinafter, various aspects and exemplary embodiments of the present disclosure are described in more detail.

In the present specification, the term "peptide" refers to a linear molecule formed as amino acid residues are linked by peptide bonds.

For reference, representative amino acids and their abbreviations are: alanine (Ala, A), isoleucine (Ile, I), leucine (Leu, L), methionine (Met, M), phenylalanine (Phe, F), proline (Pro, P), tryptophan (Trp, W), valine (Val, V), asparagine (Asn, N), cysteine (Cys, C), glutamine (Gln, Q), glycine (Gly, G), serine (Ser, S), threonine (Thr, T), tyrosine (Try, Y), aspartic acid (Asp, D), glutamic acid (Glu, E), arginine (Arg, R), histidine (His, H) and lysine (Lys, K).

An aspect of the present disclosure relates to a probe for measuring the activity of caspase-1, wherein a fluorophore (b) and a quencher (c) are bound to both ends of a polypeptide (a) consisting of 4-7 amino acid residues and being cleaved specifically by caspase-1.

In order to overcome the problems of the prior art, the inventors of the present disclosure have developed a probe capable of measuring the activity of the caspase-1 enzyme by binding a fluorophore and a quencher to a peptide sequence which is cleaved by binding specifically to the caspase-1 enzyme. Although the active caspase-1 enzyme is an important enzyme involved in inflammatory responses of various diseases, it is very difficult to measure it noninvasively and conveniently because it exists only in the cytoplasm of a cell. Therefore, in the present disclosure, in order to detect and analyze the activation of the caspase-1 enzyme existing in the cytoplasm of a cell based on fluorescence in vivo, the probe is designed such that a near-infrared fluorophore and a quencher are located within a predetermined distance (nm). If the length of the polypeptide (a) in the probe is changed (if the number of amino acid residues is smaller than 4 or larger than 7), a desired quenching effect cannot be achieved because the distance from the fluorophore and the quencher is long. This technology is advantageous in that resolution can be improved by effectively reducing background noise, thereby increasing the signal-to-noise (S/N) ratio, and that the activation or inhibition of the caspase-1 enzyme in a cell or in vivo can be imaged noninvasively in real time due to the specific reaction with the caspase-1 enzyme.

With the existing material for analysis of the activity of the caspase-1 enzyme, biological samples are obtained invasively and the activity of the caspase-1 enzyme is measured using various reagents and detection devices. The inventors have made efforts to develop a probe which can effectively infiltrate into the cytoplasm of a cell and exhibits fluorescence as it is cleaved by specifically reacting with the active caspase-1 enzyme existing in the cytoplasm, and have completed the present disclosure.

The polypeptide (a) is not specially limited as long as it is a polypeptide consisting of 4-7 amino acid residues, which is cleaved specifically by the active caspase-1 enzyme existing in the cytoplasm of a cytoplasm. Specifically, it may be any one selected from amino acid sequences represented by SEQ ID NOS 1-3. The polypeptide (a) is a polypeptide based on a peptide (WEHD (SEQ ID NO:4), LEHD (SEQ ID NO: 5) or YVAD (SEQ ID NO: 6)), wherein one or more glycine is bound to the N- and C-terminals and a lysine or arginine amino acid residue is bound to a glycine residue at the C-terminal, so that it can easily penetrate into a cell and can be cleaved (degraded) by the active caspase-1 enzyme existing in the cytoplasm of the cell.

The fluorophore (b) is bound at the N-terminal of the polypeptide (a), and the quencher (c) is bound to an ε-amine group of a lysine or arginine amino acid residue of the polypeptide (a). The probe for measuring the activity of caspase-1 is designed such that it is in quenched state and exhibits very low fluorescence intensity at normal times but exhibits fluorescence after being cleaved by the active caspase-1 enzyme existing in the cytoplasm of a cell. After infiltrating into a cell, the probe for measuring the activity of caspase-1 exhibits fluorescence as it is effectively cleaved by the active caspase-1 enzyme existing in the cell. This can be confirmed through the test examples described below.

Specifically, the quencher (c) capable of absorbing light emitted from the fluorophore (b) and exhibiting quenching effect is bound in the probe for measuring the activity of caspase-1, and strong quenching effect is achieved by absorbing the light emitted from the fluorophore (b). In other words, if the polypeptide (a) is not cleaved by the active caspase-1 enzyme existing in a cell, the quenching effect is exhibited when the distance between the fluorophore and the quencher is within tens of nanometers. If the polypeptide (a) is cleaved by the enzyme, the quenching effect disappears as the fluorophore (b) and the quencher (c) bound thereto get away from each other. As a result, the fluorophore emits intrinsic fluorescence and allows imaging of the active caspase-1 enzyme existing in the cell. Because the probe for measuring the activity of caspase-1 of the present disclosure can specifically detect only the active caspase-1 enzyme by infiltrating into the cell, the activity of caspase-1 can be measured accurately and sensitively.

Accordingly, the problems of the existing invasive analysis methods used to measure the activity of the caspase-1 enzyme can be solved, and the active caspase-1 enzyme can be detected accurately without exhibiting toxicity in vivo. Through this, various diseases related with the active caspase-1 enzyme can be diagnosed. This can be confirmed through the test examples described below.

In addition, the probe for measuring the activity of caspase-1 is absorbed easily and has excellent bioavailability because it is easily dissolved in a physiological solution. Also, it exhibits proven stability and specificity for the active caspase-1 enzyme. Therefore, it is very useful as a carrier to cells showing inflammation responses or for imaging of cells or tissues wherein the active caspase-1 enzyme is present or for screening of drugs.

The probe for measuring the activity of caspase-1 infiltrates effectively into a cell and emits fluorescence as it is cleaved by the active caspase-1 enzyme existing in the cytoplasm of the cell, thereby imaging a cell or a tissue in which the active caspase-1 enzyme exists. The cleaved probe for measuring the activity of caspase-1 does not remain in the body because it is degraded through metabolism and is excreted out of the body through the kidney. In addition, it exhibits little toxicity on its own. Therefore, it has very superior biocompatibility. This can be confirmed through the test examples described below.

The probe for measuring the activity of caspase-1 exhibits fluorescence by active caspase-1 due to inflammation responses and, therefore, allows early diagnosis of various related diseases at the same time. For example, it can diagnose cancers including squamous cell carcinoma, uterine cancer, cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, kidney cancer, bladder cancer, ovarian cancer, bile duct cancer or gallbladder cancer; dementia, stroke, and autoimmune diseases such as osteoarthritis and rheumatoid arthritis. For dementia, it is very difficult to diagnose dementia and image the related cells early before its clinical symptoms develop. However, the probe for measuring the activity of caspase-1 of the present disclosure is advantageous in that dementia can be diagnosed even before the clinical symptoms develop by measuring the active caspase-1 enzyme inducing dementia. Because various diseases are accompanied by inflammatory responses, the abnormal conditions in the body can be imaged with the probe of the present disclosure. In addition, it is advantageous in that several diseases can be diagnosed at the same time with single administration. Although the use of compositions for diagnosis is usually limited to specific diseases, the present disclosure can simultaneously detect the cells or tissues where inflammatory responses are induced throughout the body, without being limited to specific diseases, by measuring the caspase-1 enzyme generated during the process of inflammation responses.

The fluorophore (b) may be any one selected from a group consisting of fluorescein, fluorescein isothiocyanate (FITC), Oregon green, Texas red, Cy2, Cy3, Cy3B, Cy3.5, Cy5, Cy5.5, Cy7, indocarbocyanine, rhodamine, oxacarbocyanine, thiacarbocyanine, merocyanine, pyrodyloxazole, nitrobenzoxadiazole, benzoxadiazole, Nile red, Nile orange, acridine yellow, aumarine, crystal violet and malachite green.

The type of the quencher varies depending on the emission wavelength range of the fluorophore (b). It is because the quenching effect can be maximized only when the quencher has a wavelength range which is identical or almost similar to the emission wavelength of the fluorophore. In the present disclosure, the quencher may be a dark quencher capable of quenching the fluorescence of the fluorophore by absorbing the energy of the excited fluorophore but not emitting the fluorescence energy. As commercially widely applicable quenchers, any one selected from a group consisting of TAMRA (6-carboxytetramethyl-rhodamine), black hole quencher 1 (BHQ1), black hole quencher 2 (BHQ2), black hole quencher 3 (BHQ3), nonfluorescent quencher (NFQ), DABCYL, Eclipse, deep dark quencher (DDQ), BlackBerry Quencher and Iowa black may be used. For example, the wavelength region of fluorescence absorbed very effectively is 480-580 nm for BHQ-1, 550-650 nm for BHQ-2, and 620-730 nm for BHQ-3. Accordingly, when Cy5.5 (675-700 nm) is used as the fluorophore, the BHQ-3 quencher may be selected to absorb the fluorescence.

In the present disclosure, the near-infrared fluorophore Cy5.5 is introduced at the C-terminal of the polypeptide (a), and the quencher (BHQ-3) is bound to the ε-amine group (side-chain amine group) of lysine (K) or arginine located at the N-terminal. This can be achieved through various technologies well known to those skilled in the art. Specifically, the binding of the quencher (c) or the fluorophore (b) to the polypeptide (a) is conducted in DMSO in the presence of an N-methylmorpholine (NMM) and 4-dimethylaminopyridine (DMAP) catalysts. The synthesis procedure consists of fluorophore introduction, protecting group removal and quencher introduction. In each process, high-performance liquid chromatography (HPLC) is carried out for identification and purification. If an amine group is present in the polypeptide and an N-hydroxysuccinimide (NHS) functional group is present in the fluorophore and the quencher, covalent bonding is possible between the two molecules. Alternatively, if a COOH group is present in the polypeptide and an amine group is present in the fluorophore and the quencher, a crosslinker (e.g., dicyclohexylcarbodiimide (DCC) or 1-ethyl-3-(3-dimethylaminopropyl)carbodiimide (EDAC) hydrochloride) may be used to chemically bind the two residues because it is impossible to bind them directly.

As described above, the probe for measuring the activity of caspase-1 is cleaved by the active caspase-1 enzyme expressed specifically in an inflammatory cell, thereby restoring fluorescence.

If necessary, the probe for measuring the activity of caspase-1 may further include a drug or a nanoparticle. The drug or the nanoparticle may bind to a carboxyl group at the C-terminal of the polypeptide (a). Specifically, if a COOH group is present in the polypeptide (a) and an amine group is present in the drug or the nanoparticle, the COOH group of the polypeptide (a) may be reacted with sulfo-NHS (N-hydroxysulfosuccinimide) and 1-ethyl-3-(3-dimethylaminopropyl)carbodiimide (EDC) to replace it with the N-hydroxysuccinimide (NHS) functional group and then covalent bonding may be formed between the two molecules, because it is impossible to bind the two residues directly.

The probe for measuring the activity of caspase-1 is cleaved as it reacts with the active caspase-1 enzyme in the cytoplasm of a cell where inflammatory response is induced, and then fluorescence is emitted. The fluorophore is the cyanine fluorophore Cy5.5 which emits near-infrared fluorescent light (650-900 nm). As the quencher, BHQ3 which can maximize quenching effect by absorbing the fluorescence from the fluorophore may be used. The near-infrared fluorophore is suitable for in-vivo fluorescence imaging of large-sized animals such as human because it is capable of imaging cancer cells lying deeper as compared to the common fluorescent molecules emitting light in the visible region.

And, if necessary, the prepared probe for measuring the activity of caspase-1 may be subjected to purification or identification using various technologies well known to those skilled in the art.

The probe for measuring the activity of caspase-1 may be represented by the structural formula of FIG. 1A (Structural Formula 1).

fluorescence even when it is injected into the cell at a very low concentration. After injection into the cell, the intensity of fluorescence is measured at 700-900 nm using a fluorescence microscope. Because the probe for measuring the activity of caspase-1 of the present disclosure infiltrates into a cell in vivo or in vitro and emits fluorescence only in the presence of the active caspase-1 enzyme, the distribution of cells or tissues where inflammatory response is induced can be imaged effectively in a noninvasive manner. That is to say, by imaging where the inflammatory response-induced cells are distributed in an individual, the probe for measuring

[Structural Formula 1]

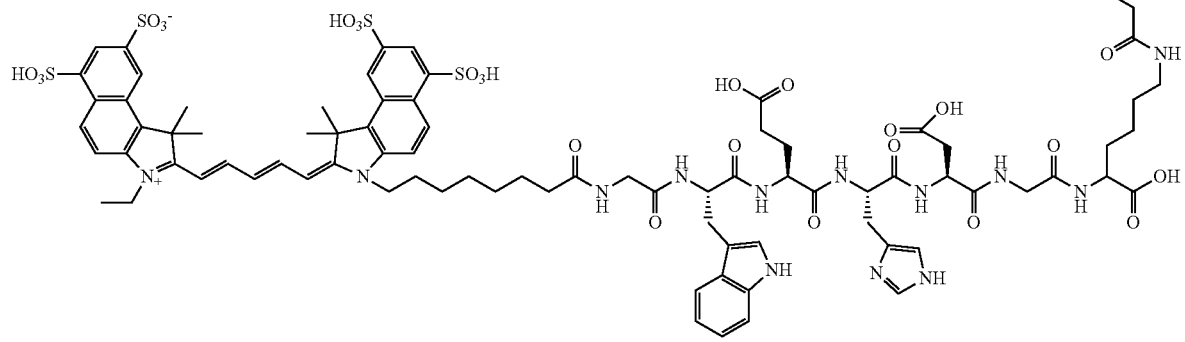

A preferable administration dosage of the probe for measuring the activity of caspase-1 of the present disclosure may be selected adequately by those skilled in the art although it varies depending on the condition and body weight of a patient, the severity of a disease, drug type, administration route and administration period. In order to achieve a desired effect, the daily administration dosage of the probe for measuring the activity of caspase-1, which is the active ingredient of the present disclosure, for a male adult may be 0.0001-100 mg/kg, specifically 0.001-60 mg/kg. The administration may be made once or several times a day. Specifically, the administration may be made with time intervals after the emission of fluorescence. The administration dosage may be adequately increased or decreased depending on the age, sex, body weight and metabolism of the patient and currently medicated other drug(s). Accordingly, the probe for measuring the activity of caspase-1 according to the present disclosure is prepared in consideration of the range of effective amount and the prepared formulation may be administered according to specialized regimen or with predetermined time intervals depending on the judgements of experts or requirements by individuals.

The probe for measuring the activity of caspase-1 of the present disclosure may be administered to a mammal such as rat, mouse, rabbit, human, etc. via various routes, e.g., orally or via intraperitoneal, intranasal, intrarectal, intravenous, intramuscular, subcutaneous or intracerebrovascular injection.

The probe for measuring the activity of caspase-1 of the present disclosure can specifically react with the active caspase-1 enzyme in the cytoplasm of a cell and emit the activity of caspase-1 of the present disclosure can be used as a composition for diagnosing inflammatory response-related diseases, diagnosing diseases in patients of early stage in which clinical symptoms have not developed, and for monitoring or prognosing therapeutic effect.

The probe for measuring the activity of caspase-1 of the present disclosure can be prepared into a single-dosage or multi-dosage formulation using a pharmaceutically acceptable carrier and/or excipient according to a method that can be easily carried out by those of ordinary skill in the art to which the present disclosure belongs. The formulation may be in the form of a solution, suspension or emulsion in an oily or aqueous medium, an extract, a powder, a granule, a tablet, a capsule, etc. and may further contain a dispersant or a stabilizer.

Another aspect of the present disclosure relates to a composition for qualitatively or quantitatively analyzing the caspase-1 enzyme expressed in a cell or a tissue, which contains the probe for measuring the activity of caspase-1 as an active ingredient, and a composition for screening a drug inhibiting the activation of the caspase-1 enzyme, which contains the probe for measuring the activity of caspase-1 as an active ingredient. The probe for measuring the activity of caspase-1 may be used for various purposes, such as for imaging of cells or tissues where inflammatory response is induced, as a drug carrier, for screening of a drug inhibiting inflammatory response, etc., because the presence of the active caspase-1 enzyme existing in a tissue or the cytoplasm of a cell, its activity, inhibition of the activity, can be determined easily. The composition is applicable both in vivo and in vitro, and can be used for various applications such as high-throughput screening for new drug development, early diagnosis of diseases, etc.

Specifically, the composition may be used to provide information for diagnosing diseases related with inflammatory responses, investigating the effect of a drug effective in inhibiting inflammatory response, predicting the reactivity for a specific drug in advance or identifying the location of inflammatory cells by administering it to an individual suspected with a disease related with inflammatory response (or activation of the caspase-1 enzyme) and monitoring the presence and distribution of cells or tissues where inflammatory response is induced. These are very important with regard to early diagnosis and early treatment of diseases.

The disease to which the protein-fluorophore complex of the present disclosure can be applied may be any disease related with the caspase-1 enzyme. Usually, it may be a cancer disease, an autoimmune disease or an inflammatory disease, although not being specially limited thereto. For example, it may be a cancer including squamous cell carcinoma, uterine cancer, cervical cancer, prostate cancer, head and neck cancer, pancreatic cancer, brain tumor, breast cancer, liver cancer, skin cancer, esophageal cancer, testicular cancer, kidney cancer, colon cancer, rectal cancer, stomach cancer, kidney cancer, bladder cancer, ovarian cancer, bile duct cancer or gallbladder cancer, dementia, stroke, or an autoimmune disease such as osteoarthritis and rheumatoid arthritis.

A preferable administration dosage of the composition may be selected adequately by those skilled in the art although it varies depending on the condition and body weight of a patient, the severity of a disease, drug type, administration route and administration period. In order to achieve a desired effect, the daily administration dosage of the probe for measuring the activity of caspase-1, which is the active ingredient of the present disclosure, for a male adult may be 0.0001-100 mg/kg, specifically 0.001-60 mg/kg. The administration may be made once or several times a day. Specifically, the administration may be made with time intervals after the emission of fluorescence. The administration dosage may be adequately increased or decreased depending on the age, sex, body weight and metabolism of the patient and currently medicated other drug(s). Accordingly, the probe for measuring the activity of caspase-1 according to the present disclosure is prepared in consideration of the range of effective amount and the prepared formulation may be administered according to specialized regimen or with predetermined time intervals depending on the judgements of experts or requirements by individuals.

The probe for measuring the activity of caspase-1 of the present disclosure may be administered to a mammal such as rat, mouse, rabbit, human, etc. via various routes, e.g., orally or via intraperitoneal, intranasal, intrarectal, intravenous, intramuscular, subcutaneous or intracerebrovascular injection.

The probe for measuring the activity of caspase-1 in the composition emits fluorescence as it is cleaved by the active caspase-1 enzyme existing in the cytoplasm of a cell. Through this, it is possible to image the cells or tissues where inflammatory response is induced or to investigate whether a drug is delivered successfully to the cells where inflammatory response is induced.

Another aspect of the present disclosure relates to a method for imaging cells or tissues where inflammatory response is induced, which includes: 1) a step of administering the probe for measuring the activity of caspase-1 to an individual; and 2) a step of acquiring an image obtained due to the probe for measuring the activity of caspase-1 from the individual.

In the method, if a region where fluorescence is emitted is observed from the image, it can be determined that a cell where inflammatory response is induced exists and the location of the cell where inflammatory response is induced can be identified.

After administering a drug expected to inhibit inflammatory response and performing measurement according to the above-described method, if the fluorescence region is decreased or not increased in the image, the drug may be determined to have a positive effect of inhibiting inflammatory response. And, if the fluorescence region is increased, the drug may be determined to have a negative therapeutic effect.

The individual may be a mammal such as rat, mouse, rabbit, human, etc., and the administration may be made orally or via intraperitoneal, intranasal, intrarectal, intravenous, intramuscular, subcutaneous or intracerebrovascular injection.

Hereinafter, the present disclosure will be described in more detail through various examples. However, the scope of this disclosure should not be construed as being limited by the examples. In addition, it will be obvious that the present disclosure about which experimental results are not described specifically can be carried out easily by those of ordinary skill based on the description of the present disclosure including the examples and that such change and modification belong to the scope defined in the appended claims.

Examples 1-3. Synthesis of Polypeptide (a)

Polypeptides represented by SEQ ID NOS 1-3 (Examples 1-3, respectively) were designed and prepared by solid-phase peptide synthesis (SPPS). They were prepared by sequentially attaching Fmoc-protected amino acid monomers to Rink amide resin where amide was fixed at the C-terminal according to the designed polypeptide sequence. In order to ensure 1:1 binding between amine and sulfo-NHS of the polypeptide, a tert-butyloxycarbonyl (BOC) protecting group was bonded to the lysine (K) or arginine (R) residue.

```
                                          [SEQ ID NO 1]
          GWEHDGK

[SEQ ID NO 2]
          GLEHDGK

[SEQ ID NO 3]
          GYVADGK
```

The synthesized polypeptide was purified by reversed-phase HPLC (Shimadzu Prominence HPLC, Japan) using the Vydac Everest C18 column (250 mm×22 mm, 10 μm, USA). Elution was carried out using a water-acetonitrile linear gradient (5-95% (v/v) of acetonitrile) containing 0.1% (v/v) trifluoroacetic acid. The purified polypeptide was lyophilized using FDT12012 (Operon, Korea). The polypeptide was designed to be cleavable by lysosomal degradative enzymes in cells. Specifically, the backbone was a peptide with a sequence of WEHD (SEQ ID NO: 4), LEHD (SEQ ID NO:5) or YVAD (SEQ ID NO: 6), and one glycine was bound to the N-terminal and one or more glycine and lysine (K) amino acid residue was bound to the C-terminal.

Examples 4-6. Preparation of Probe for Measuring Activity of Caspase-1

A probe was designed such that the near-infrared fluorophore Cy5.5 was bound to the N-terminal of one of the polypeptides (SEQ ID NOS 1-3) synthesized in Examples 1-3 and the quencher BHQ-3 was bound to the ε-amine group of the lysine amino acid residue of the polypeptide. A detailed synthesis procedure is as follows.

The synthesis procedure consisted three steps of fluorophore introduction, protecting group removal and quencher introduction. Each synthesis procedure was conducted in DMSO in the presence of N-methylmorpholine (NMM) and 4-dimethylaminopyridine (DMAP) catalysts. After each synthesis process, high-performance liquid chromatography (HPLC) was carried out for identification and purification, and the product was lyophilized and stored in a refrigerator.

1) Introduction of Fluorophore 10 mg of the polypeptide of Example 1, 2 or 3 (SEQ ID NOS 1-3) was mixed with 12 mg of the near-infrared fluorophore Cy5.5-NHS, 10 μL of N-methylmorpholine (NMM), 0.5 mg of 4-dimethylaminopyridine (DMAP) and 200 μL dimethylformamide, and reaction was carried out at room temperature for 4 hours. After the reaction was completed, the reaction solution was purified by high-performance liquid chromatography (HPLC). The HPLC purification was conducted using a cocktail solution (0.1% trifluoroacetic acid (TFA)/acetonitrile, 0.1% trifluoroacetic acid/distilled water), with a ratio of 5%:95% from 0 to 5 minutes and with various ratios (95%, 5%) to 25 minutes. After removing the solvent using an evaporator, the purified solution was lyophilized under vacuum and stored as a powder state.

2) Removal of Protecting Group

In order to remove the BOC protecting group present in the lysine residue of the Cy5.5 (fluorophore)-bound polypeptide synthesized in the step 1), a mixture solution of 950 μL of trifluoroacetic acid, 25 μL of distilled water and 25 μL of anisole was added and reaction was conducted for 1 hour at room temperature. After completely removing the solvent using an evaporator, the residue was dissolved in 1 mL of a cocktail solution (0.1% trifluoroacetic acid/acetonitrile: 0.1% trifluoroacetic acid/distilled water=1:1) and purified with a 0.2-μm filter. The purified solution was purified by HPLC using the Agilent ZORBAX SB-C18 column (9.4× 150 mm) for 30 minutes with a concentration gradient of 0.1% TFA/acetonitrile, 0.1% TFA/95% distilled water. The product was identified with UV at a wavelength of 220 nm (fluorescence ex: 675 nm, em: 695 nm). The identified product was subjected to molecular weight measurement by mass spectroscopy and then lyophilized.

3) Introduction of Quencher

BHQ3-NHS (Black Hole Quencher 3-NHS) was bound to the ε-amine group of the exposed lysine (K) of the Cy5.5 (fluorophore)-bound polypeptide with the protecting group removed, which was obtained in the step 2). For this, 2 mg of the Cy5.5 (fluorophore)-bound polypeptide with the protecting group removed, obtained in the step 2), 0.71 mg of BHQ3-NHS (Biosearch Technologies Inc.), 2 μL of N-methylmorpholine (NMM), 0.2 mg of 4-dimethylaminopyridine (DMAP) and 30 μL of dimethyl sulfoxide (DMSO) were mixed and reaction was conducted at room temperature for 4 hours to prepare a probe for measuring the activity of caspase-1. The probe for measuring the activity of caspase-1 was purified by HPLC under the same condition as described above, and the purified product was subjected to molecular weight measurement by mass spectroscopy and then lyophilized.

Test Example 1. Confirmation of Synthesis of Probe for Measuring Activity of Caspase-1

The synthesis and performance of the probe for measuring the activity of caspase-1 prepared in Example 4 were confirmed as follows.

Figure 2A:
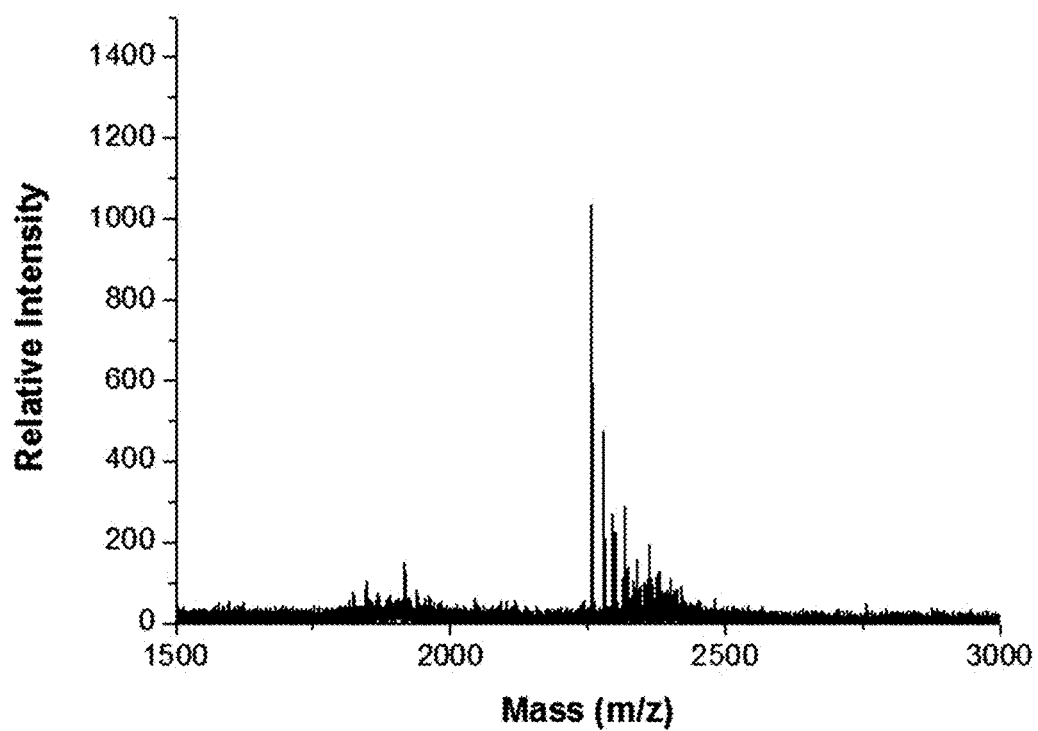
FIG. 2A shows a result of measuring the molecular weight of a probe for measuring the activity of caspase-1 prepared in Example 4 by matrix-assisted laser desorption/ionization time-of-flight mass spectrometry (MALDI-TOF MS).

FIG. 2A shows a result of measuring the molecular weight of the probe for measuring the activity of caspase-1 prepared in Example 4 by matrix-assisted laser desorption/ionization time-of-flight mass spectrometry (MALDI-TOF MS).

As seen from FIG. 2A, the binding of the fluorophore and the quencher was confirmed through the matrix-assisted laser desorption/ionization time-of-flight mass spectrometry (MALDI-TOF MS) analysis. That is to say, it was confirmed that the probe for measuring the activity of caspase-1 prepared in Example 4 was synthesized as the fluorophore (b) and the quencher (c) were bound to the polypeptide (a). As a result of the mass spectroscopic analysis, the probe for measuring the activity of caspase-1 prepared in Example 4 had a molecular weight of 2255 as expected. Therefore, it was confirmed that the probe has a structure wherein the polypeptide (a), the fluorophore (b) and the quencher (c) are bound.

Figure 2B:
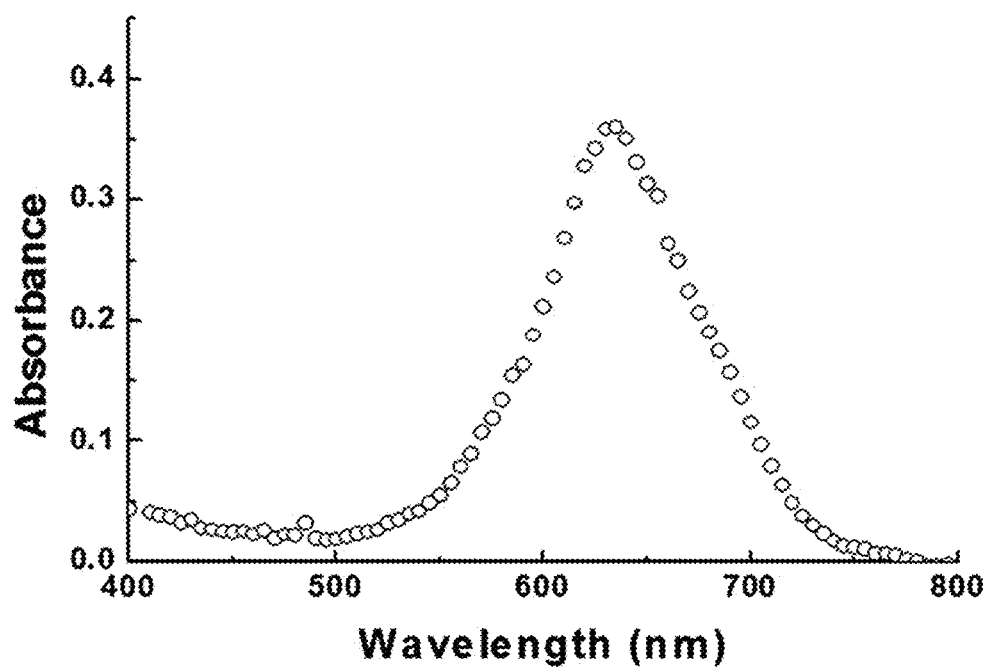
FIG. 2B shows the ultraviolet-visible (UV-Vis) spectroscopic analysis result of a probe for measuring the activity of caspase-1 prepared in Example 4.

FIG. 2B shows the ultraviolet-visible (UV-Vis) spectroscopic analysis result of the probe for measuring the activity of caspase-1 prepared in Example 4. The UV-Vis spectroscopy reveals binding between the materials by analyzing the intrinsic wavelength ranges of the quencher and the fluorophore. As seen from FIG. 2B, the probe for measuring the activity of caspase-1 prepared in Example 4 showed the peak of the quencher at 660 nm and the peak of the fluorophore at 680 nm.

Figure 2C:
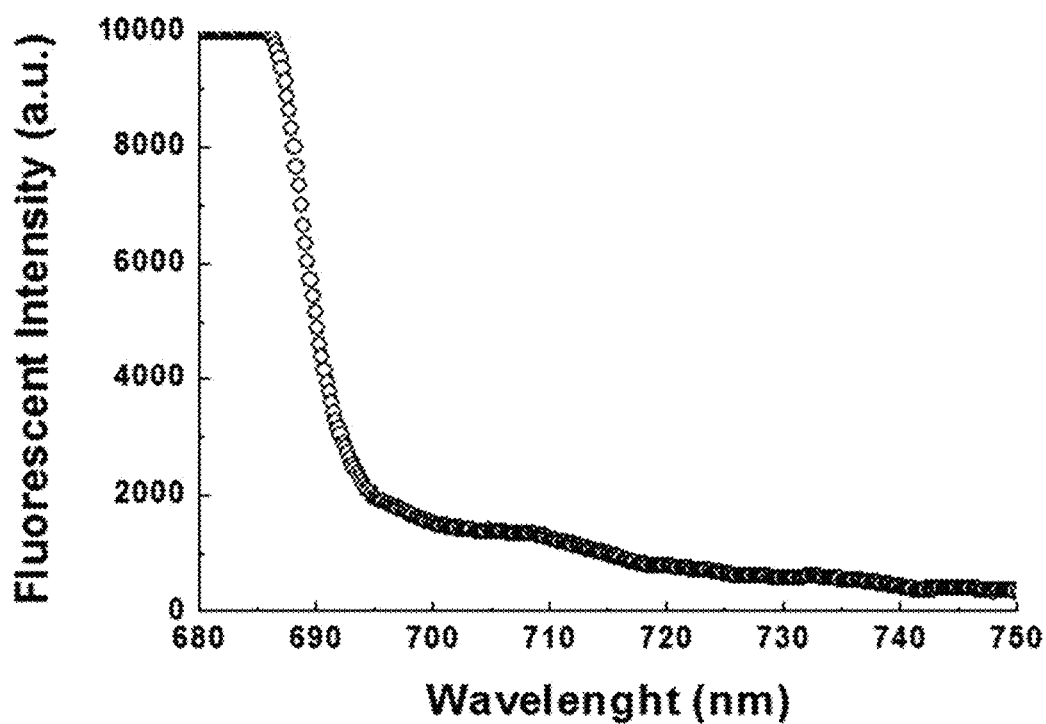
FIG. 2C shows a fluorescence spectroscopic analysis result of a probe for measuring the activity of caspase-1 prepared in Example 4.

FIG. 2C shows a fluorescence spectroscopic analysis result of the probe for measuring the activity of caspase-1 prepared in Example 4. It was confirmed that the quencher absorbs fluorescence effectively. That is to say, it was confirmed that the probe for measuring the activity of caspase-1 prepared in Example 4 effectively absorbs fluorescence at 680-700 nm, which corresponds to the wavelength range of the fluorophore.

To summarize, it was confirmed that the probe for measuring the activity of caspase-1 prepared in Example 4 was synthesized well.

Test Example 2. Analysis of Specific Activity of Probe for Measuring Activity of Caspase-1

In order to investigate whether the probe for measuring the activity of caspase-1 prepared in Example 4 is specifically cleaved by the caspase-1 enzyme and restores fluorescence, the change in fluorescence with time was analyzed and evaluated using various caspase enzymes (caspase-1, 3, 8 and 11) and a caspase-1 inhibitor.

First, a caspase enzyme or a caspase-1 inhibitor was dissolved in a reaction buffer (0.5 mM HEPES, pH 7.2, 50 mM calcium chloride, 0.1% CHAPS, 10 mM EDTA, 5% glycerol, 10 mM DTT) and then incubated at 37° C. for 1 hour. All the enzymes were used at the same concentration of 2 units. After transferring 200 μL of the caspase enzyme activated through the procedure to each well of a 96-well plate and then incubating with the probe for measuring the activity of caspase-1 of Example 4 at 37° C., the restoration of fluorescence with time was observed by fluorescence spectroscopy.

Figure 3A:
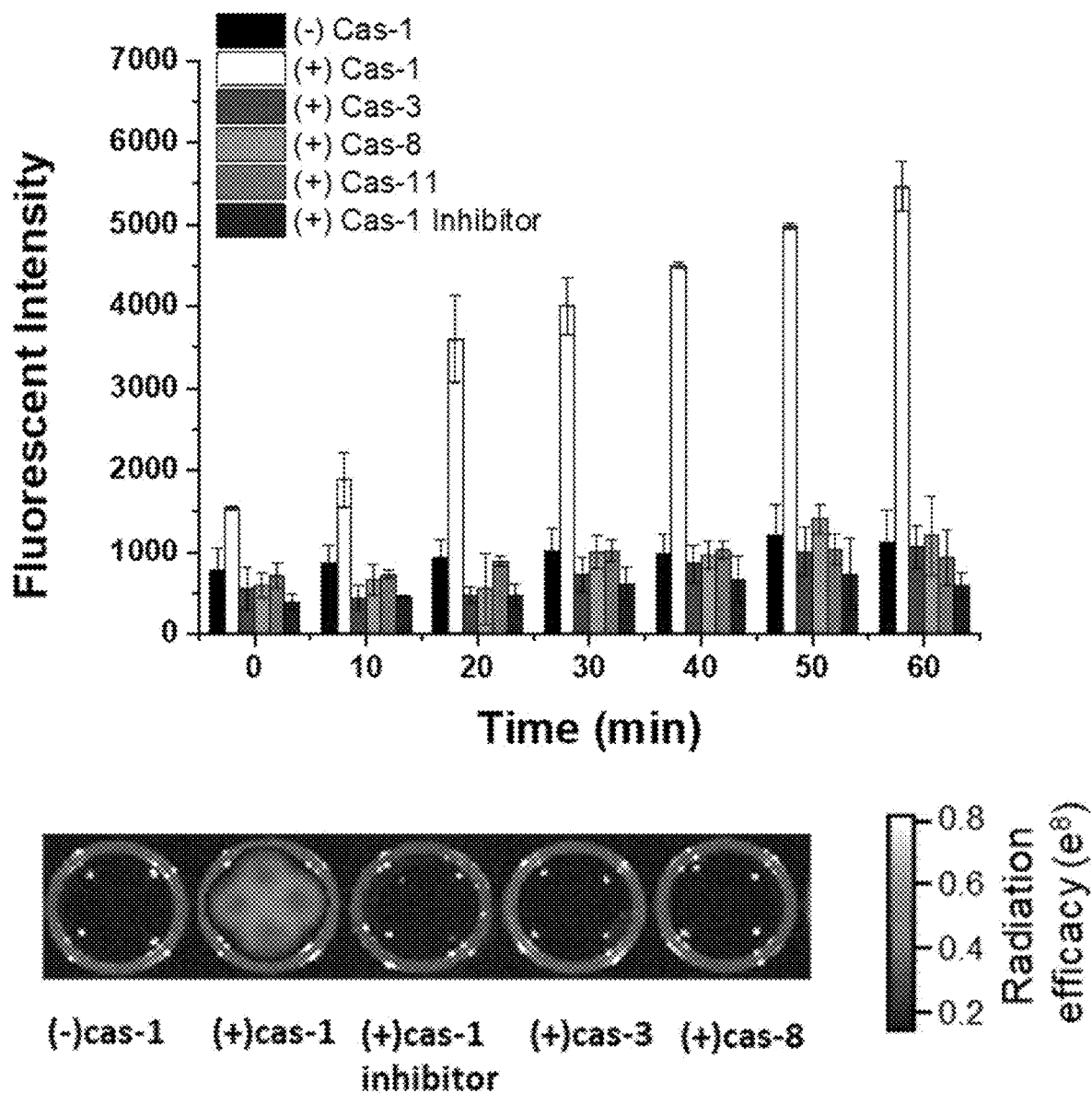
FIG. 3A shows a result of treating with a probe for measuring the activity of caspase-1 prepared in Example 4 and caspase enzymes (caspase-1, 3, 8 or 11) or a caspase-1 inhibitor and measuring the restoration of fluorescence with time by photoluminescence (PL).

FIG. 3A shows a result of treating with the probe for measuring the activity of caspase-1 prepared in Example 4 and caspase enzymes (caspase-1, 3, 8 or 11) or a caspase-1 inhibitor and measuring the restoration of fluorescence with time by photoluminescence (PL). The photographs at the bottom of FIG. 3A show the fluorescence images of the respective reaction solutions. (+)Cas-1 was treated with the caspase-1 enzyme, (+)cas-1 inhibitor was treated with the caspase-1 inhibitor, (+)cas-3 was treated with the caspase-3 enzyme, (+)cas-8 was treated with the caspase-8 enzyme, and (+)cas-11 was treated with the caspase-11 enzyme.

As seen from FIG. 3A, it was confirmed that the probe for measuring the activity of caspase-1 prepared in Example 4 restores fluorescence specifically only in the presence of caspase-1 at all times.

Test Example 3. Analysis of Probe for Measuring Activity of Caspase-1 Depending on Enzyme Concentration In order to investigate the fluorescence of the probe for measuring the activity of caspase-1 prepared in Example 4 depending on the concentration of the caspase-1 enzyme, the change in fluorescence with time was analyzed and evaluated using the caspase-1 enzyme at various concentrations (0, 2.5, 5, 7.5 and 10 units).

First, the caspase enzyme of various concentrations (0, 2.5, 5, 7.5 and 10 units) was dissolved in a reaction buffer (0.5 mM HEPES, pH 7.2, 50 mM calcium chloride, 0.1% CHAPS, 10 mM EDTA, 5% glycerol, 10 mM DTT) and incubated at 37° C. for 1 hour. After transferring 200 μL of the caspase enzyme activated through the procedure to each well of a 96-well plate and then incubating with the probe for measuring the activity of caspase-1 of Example 4 at 37° C., the restoration of fluorescence with time was observed by fluorescence spectroscopy.

Figure 3B:
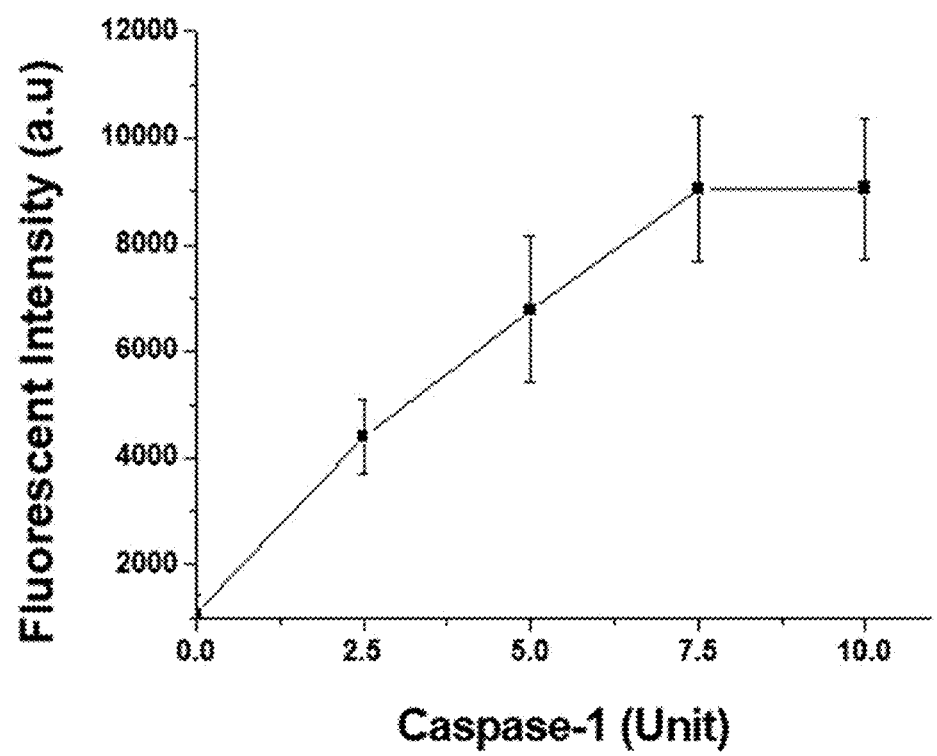
FIG. 3B shows a result of treating with a probe for measuring the activity of caspase-1 prepared in Example 4 and the caspase-1 enzyme at different concentrations (0, 2.5, 5, 7.5 and 10 units) and measuring the restoration of fluorescence with time by photoluminescence (PL). The fluorescence image for each reaction solution is shown at the bottom of FIG. 3B.
Figure 3B:
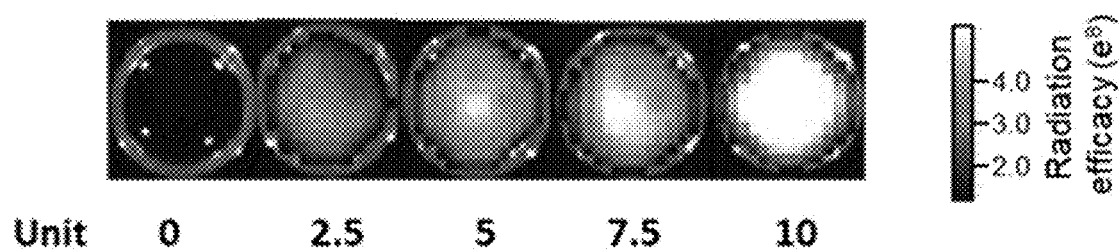

FIG. 3B shows a result of treating with the probe for measuring the activity of caspase-1 prepared in Example 4 and the caspase-1 enzyme at different concentrations (0, 2.5, 5, 7.5 and 10 units) and measuring the restoration of fluorescence with time by photoluminescence (PL). The fluorescence image for each reaction solution is shown at the bottom of FIG. 3B.

As seen from FIG. 3B, it was confirmed that the probe for measuring the activity of caspase-1 prepared in Example 4 shows increase in fluorescence intensity as the concentration of the caspase-1 enzyme increases. The concentration limit of the caspase-1 enzyme that could be measured with the probe for measuring the activity of caspase-1 prepared in Example 4 was 7.5 units. Above 7.5 units, dilution is preferred for accurate measurement of concentration.

Test Example 4. Cytotoxicity of Probe for Measuring Activity of Caspase-1

Monocytes (THP-1) and bone marrow-derived macrophages (BMDM) were placed on a 96-well plate. One day later, the probe for measuring the activity of caspase-1 (Example 4) at various concentrations (0-50 μg/mL) was administered for 24 hours. Then, cell viability was measured using a CCK-8 solution to identify the toxicity of the probe for measuring the activity of caspase-1.

Figure 4A:
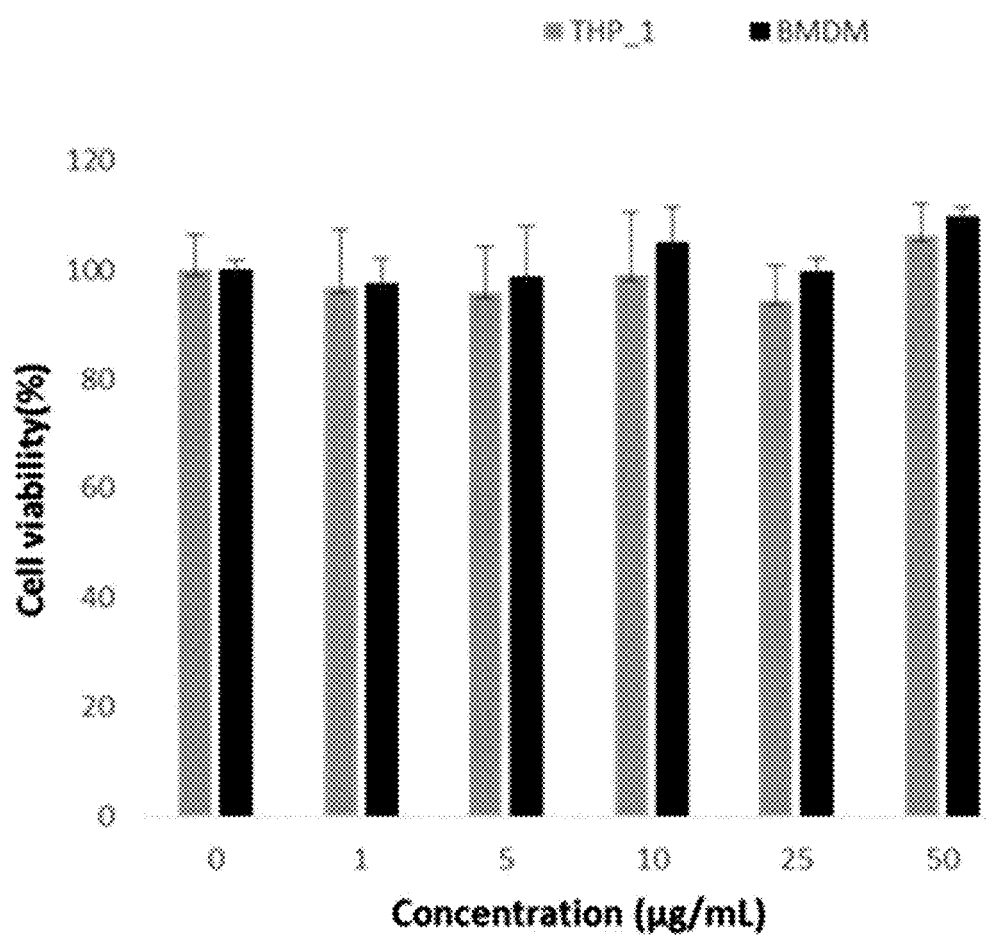
FIG. 4A shows the cell viability of THP-1 cells and BMDM cells treated with a probe for measuring the activity of caspase-1 prepared in Example 4 at different concentrations (0-50 μg/mL).

FIG. 4A shows the cell viability of the THP-1 cells and the BMDM cells treated with the probe for measuring the activity of caspase-1 prepared in Example 4 at different concentrations (0-50 μg/mL). It can be seen that the probe for measuring the activity of caspase-1 of Example 4 does not exhibit toxicity to the cells.

Test Example 5. Analysis of Effect of Fluorescence Restoration in Cells by Probe for Measuring Activity of Caspase-1

THP-1 monocytes were placed on a 96-well plate and treated with 1.5 μg/mL LPS and 5 mM ATP one day later. 3.5 hours later, the probe for measuring the activity of caspase-1 prepared in Example 4 was administered. Then, after culturing for 24 hours, fluorescence restoration by the probe for measuring the activity of caspase-1 in the cells was analyzed with a fluorescence microscope.

Figure 4B:
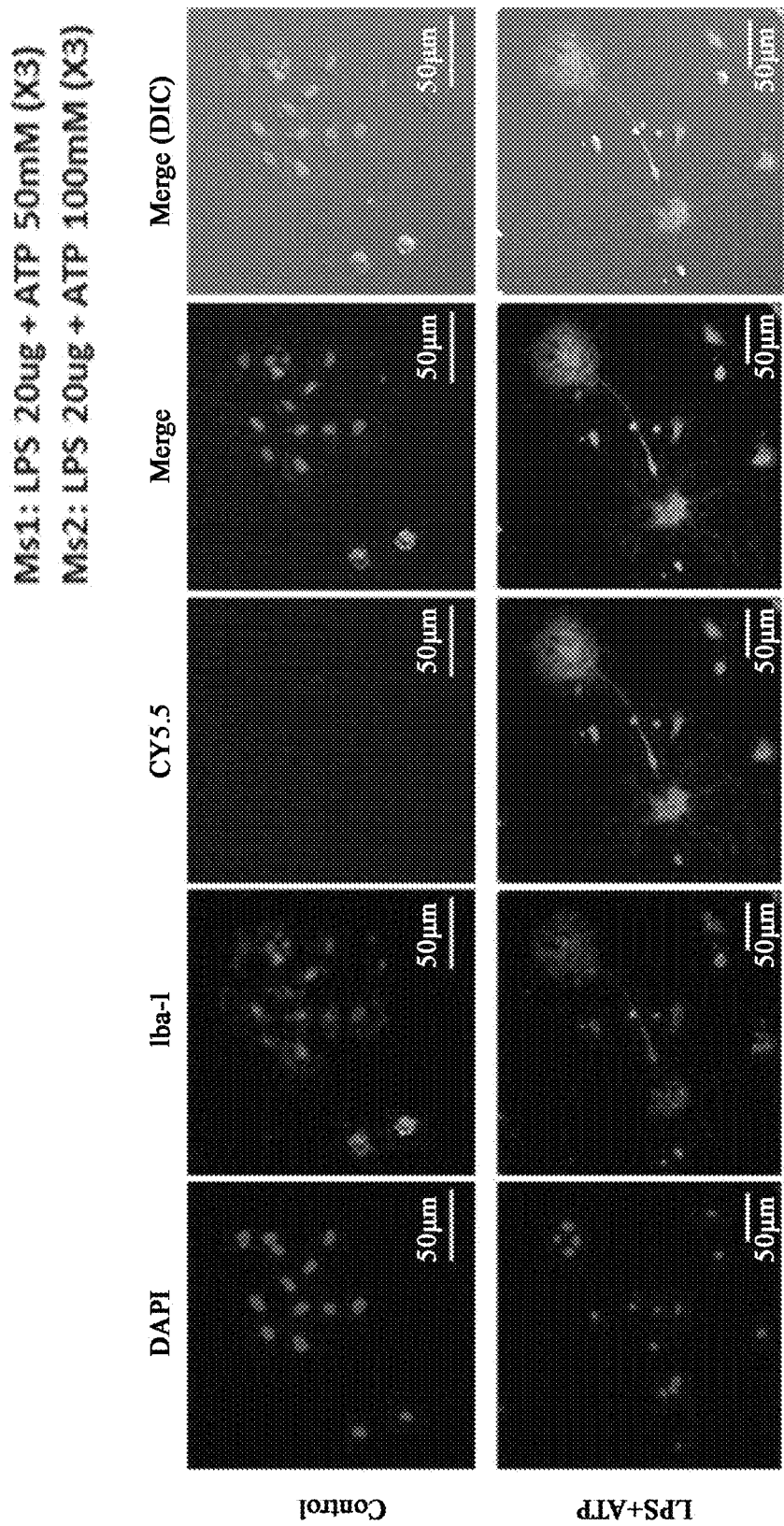
FIG. 4B shows a result of treating THP-1 cell with 1.5 μg/mL LPS and 5 mM ATP, treating with a probe for measuring the activity of caspase-1 prepared in Example 4 3.5 hours later for 30 minutes, and imaging the cells with a fluorescence microscope. Control is treated with neither LPS nor ATP.

FIG. 4B shows a result of treating the THP-1 cell with 1.5 μg/mL LPS and 5 mM ATP, treating with the probe for measuring the activity of caspase-1 prepared in Example 4 3.5 hours later for 30 minutes, and imaging the cells with a fluorescence microscope. Control was treated with neither LPS nor ATP.

As seen from FIG. 4B, after treating the THP-1 monocytes with lipopolysaccharide (LPS) and adenosine triphosphate (ATP) for 3 hours, the cells were treated with the probe for measuring the activity of caspase-1 of Example 4 for 30 minutes and then observed with a fluorescence microscope. LPS and ATP are known to activate caspase-1. LPS is a primary signal occurring in the early stage of inflammation and ATP is a secondary signal. When the cells administered with the inflammation-inducing substances were treated with the probe for measuring the activity of caspase-1 of Example 4, the fluorescence of Cy5.5 was restored effectively as compared to the control group. That is to say, it was confirmed that the probe for measuring the activity of caspase-1 of the present disclosure can accurately measure caspase-1 activated by inflammation response.

Test Example 6. Detection of Inflammation in Mouse Using Probe for Measuring Activity of Caspase-1

The caspase-1 enzyme is activated due to various factors. Among them, the most representative method is to activate inflammasome by administering LPS or ATP which induces early inflammation response. In Test Example 5, it was confirmed using the probe for measuring the activity of caspase-1 of Example 4 that the administration of LPS and ATP induced the activation of inflammasome, which is an early inflammation response. In this test example, an experiment was carried out using an inflammation-induced animal model in order to investigate whether the probe for measuring the activity of caspase-1 of Example 4 works well in vivo, too.

In order to establish the inflammation-induced animal model, 8-week-old C57BL/6 mice acquired from Nara Bio were accustomed for a week and then reared in animal plastic cages, with 4 mice per cage. The cage was controlled with artificial lighting for 12 hours from 7 am to 7 μm, indoor temperature of 18-23° C. and 40-60% humidity. Clean water and feed were given freely. Then, physiological saline (control group), 20 μg of LPS and 50 mM ATP (Ms1 test group) or 20 μg of LPS and 100 mM ATP (Ms2 test group) was injected into the left sole of the experimental animal. After intravenously injecting the probe for measuring the activity of caspase-1 prepared in Example 4 with 3-day intervals, the respective groups were imaged with IVIS Lumina with 30-minute intervals.

Figure 5A:
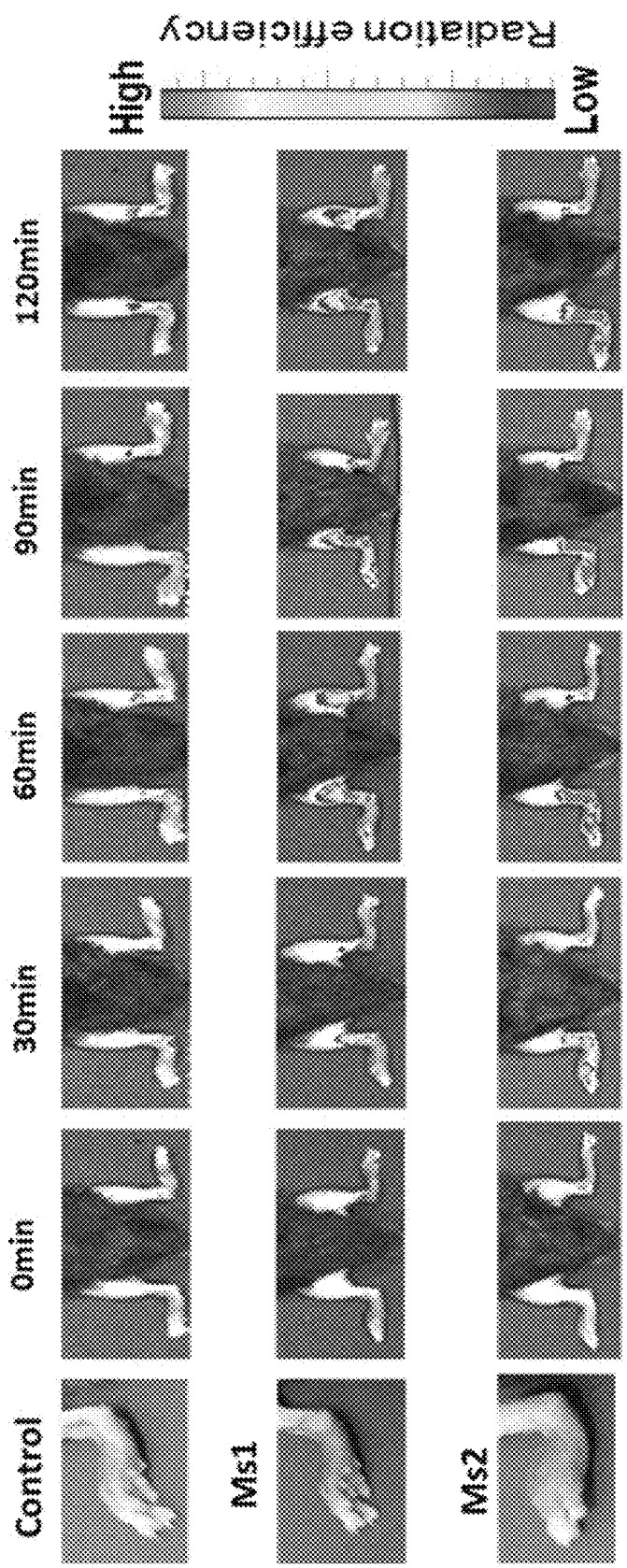
FIG. 5A shows images of a control group, an Ms1 test group and an Ms2 test group of an inflammation-induced animal model obtained with IVIS Lumina.
Figure 5B:
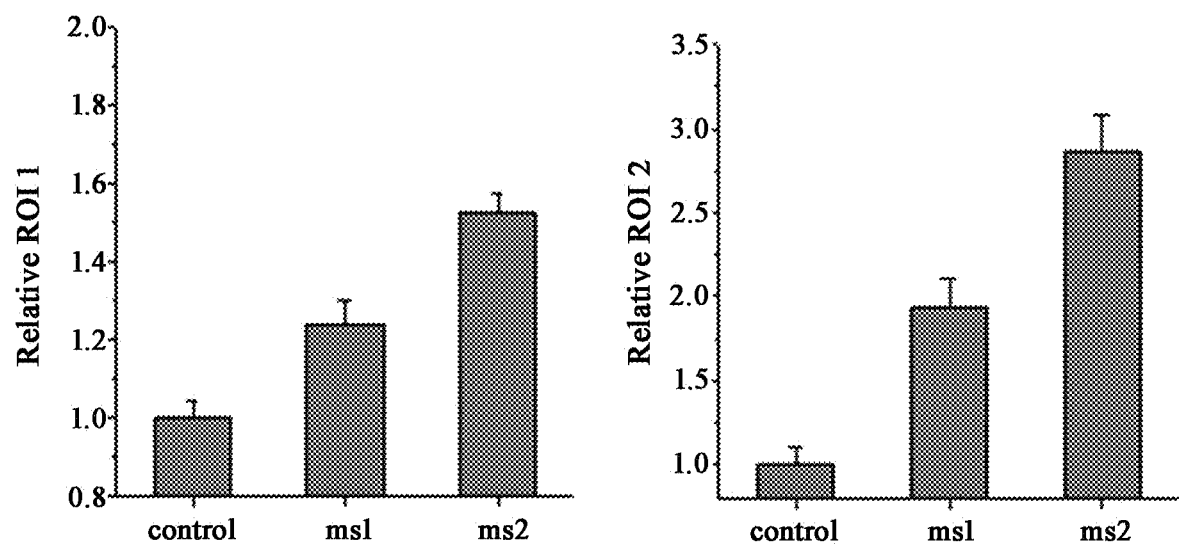
FIG. 5B shows a result of quantifying the fluorescence from the top of the left foot of a control group, an Ms1 test group and an Ms2 test group (left graph), and a result of quantifying the fluorescence from the left calf of a control group, an Ms1 test group and an Ms2 test group (right graph).

FIG. 5A shows the images of the control group, the Ms1 test group and the Ms2 test group of the inflammation-induced animal model obtained with IVIS Lumina, and FIG. 5B shows a result of quantifying the fluorescence from the top of the left foot of the control group, the Ms1 test group and the Ms2 test group (left graph), and a result of quantifying the fluorescence from the left calf of the control group, the Ms1 test group and the Ms2 test group (right graph).

As seen from FIG. 5A, it was confirmed that inflammation response was stronger as the concentration of the inflammation-inducing substances (LPS, ATP) was stronger and that the fluorescence was restored better by the probe for measuring the activity of caspase-1 of Example 4. That is to say, it was confirmed that the probe for measuring the activity of caspase-1 of the present disclosure exhibits strong fluorescence in response to strong inflammatory response (inflammation-inducing substances of higher concentration).

As seen from FIG. 5B, it was confirmed that the Ms2 test group wherein relatively stronger inflammatory response was induced through administration of the inflammation-inducing substance at higher concentration exhibits stronger fluorescence. That is to say, it was demonstrated that the probe for measuring the activity of caspase-1 of the present disclosure exhibits increased fluorescence depending on the concentration of the inflammation-inducing substance and allows accurate monitoring under an in-vivo environment in an animal model in a noninvasive manner.

Figure 5C:
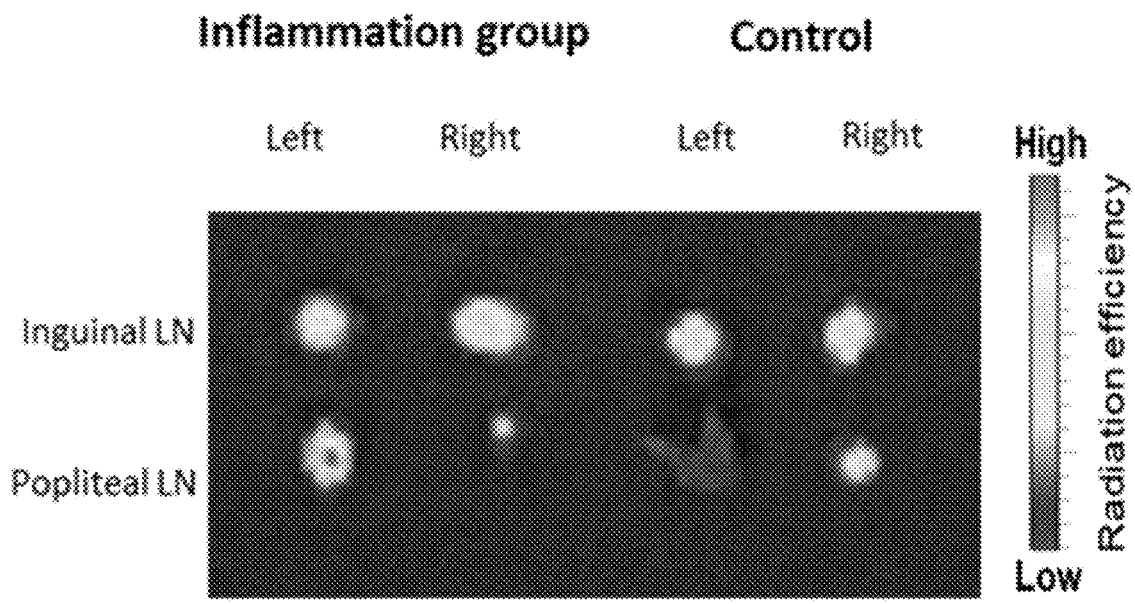
FIG. 5C shows a result of observing fluorescence from the groin, ham and lymph node of a control group, an Ms1 test group and an Ms2 test group of an inflammation-induced animal model.

FIG. 5C shows a result of observing fluorescence from the groin, ham and lymph node of the control group, the Ms1 test group and the Ms2 test group of the inflammation-induced animal model. The strongest fluorescence was observed in the ham lymph node closest to the sole of the inflammation-induced mouse (animal model). Through this, it can be seen that the inflammatory region can be observed with the probe for measuring the activity of caspase-1 of Example 4.

Test Example 7. Analysis of Colitis Animal Model Using Probe for Measuring Activity of Caspase-1

In order to establish a colitis animal model, 8-week-old C57BL/6 mice acquired from Nara Bio were accustomed for a week and then reared in animal plastic cages, with 4 mice per cage. The cage was controlled with artificial lighting for 12 hours from 7 am to 7 pm, indoor temperature of 18-23° C. and 40-60% humidity. Clean water and feed were given freely. Colitis was induced by providing the experimental animal with drinking water containing 3% dextran sodium sulfate (DSS). The colitis animal model shows shortened colon length and bloody excrement with time due to worsened inflammation in the large intestine. Because the body weight of the colitis animal model decreases proportionally to the progress of the disease, the probe for measuring the activity of caspase-1 of Example 4 was administered on day 6, when the body weight was decreased to 80%, for imaging. As a control group (normal), a non-colitis-induced group was prepared by providing normal drinking water to the experimental animal.

Figure 6A:
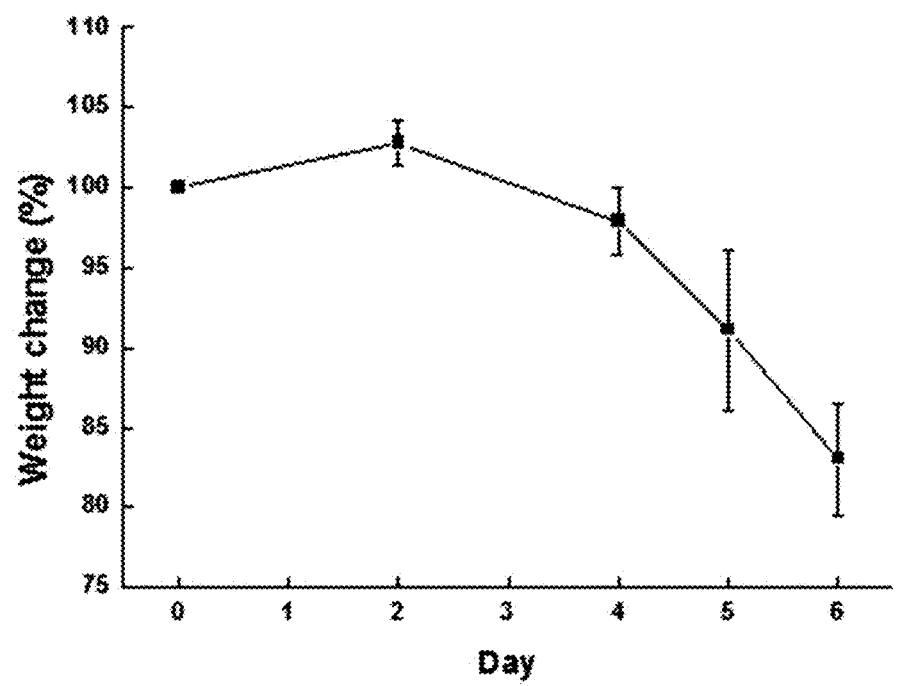
FIG. 6A shows a result of measuring body weight change of a colitis animal model with time.

FIG. 6A shows a result of measuring body weight change of the colitis animal model with time. It was confirmed that the body weight was decreased gradually with the progress of the disease and decreased to 80% on day 6.

Figure 6B:
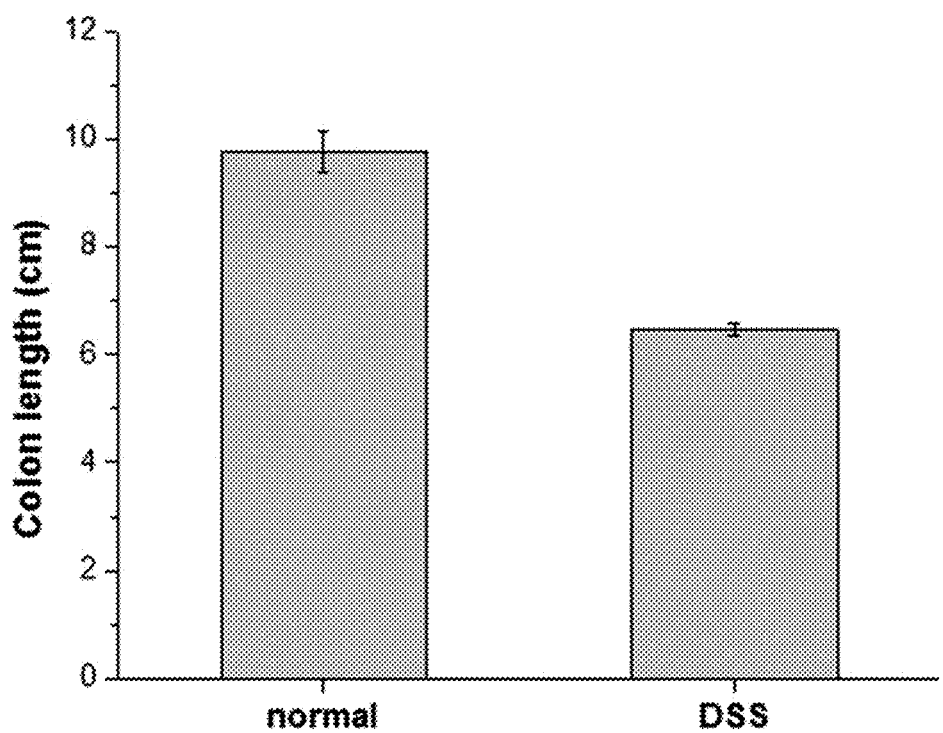
FIG. 6B shows a result of measuring the colon length (cm) of a colitis animal model (DSS) and a control group (normal).

FIG. 6B shows a result of measuring the colon length (cm) of the colitis animal model (DSS) and the control group (normal). It was confirmed that colitis was induced in the experimental anima through the above-described procedure.

Figure 6C:
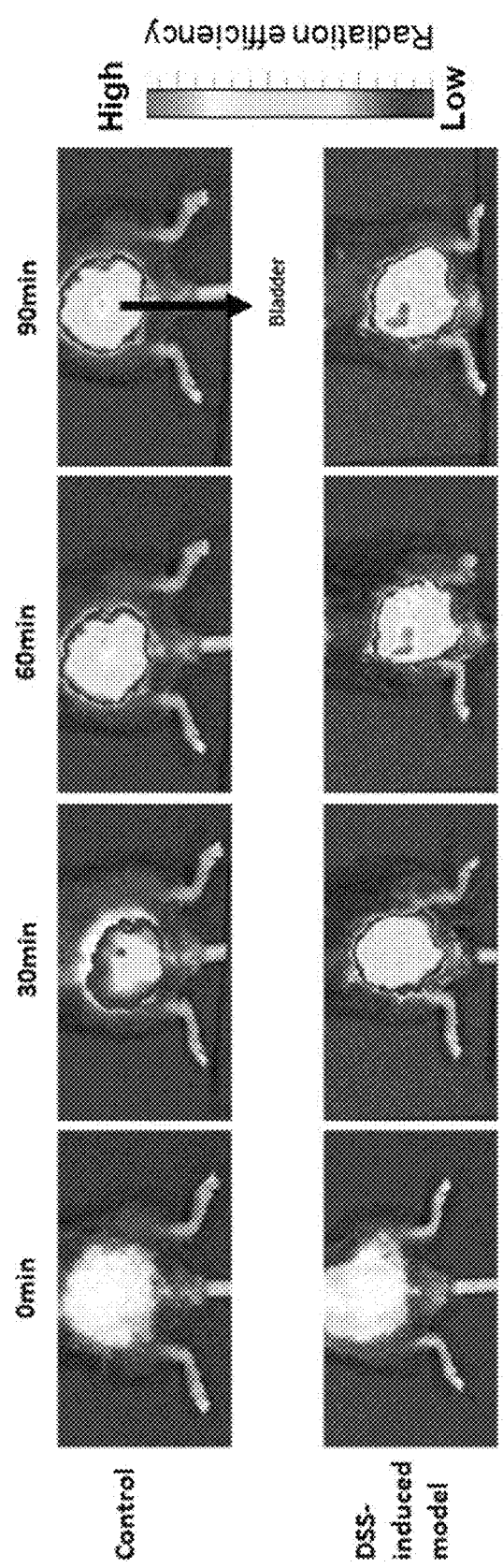
FIG. 6C shows fluorescence images obtained with 30-minute intervals after intravenously injecting a probe for measuring the activity of caspase-1 prepared in Example 4 to a colitis animal model (DSS) and a control group (normal).

FIG. 6C shows the fluorescence images obtained with 30-minute intervals after intravenously injecting the probe for measuring the activity of caspase-1 prepared in Example 4 to the colitis animal model (DSS) and the control group (normal). As seen from FIG. 6C, red fluorescence was observed clearly in the colitis animal model due to excessive inflammation.

Figure 6D:
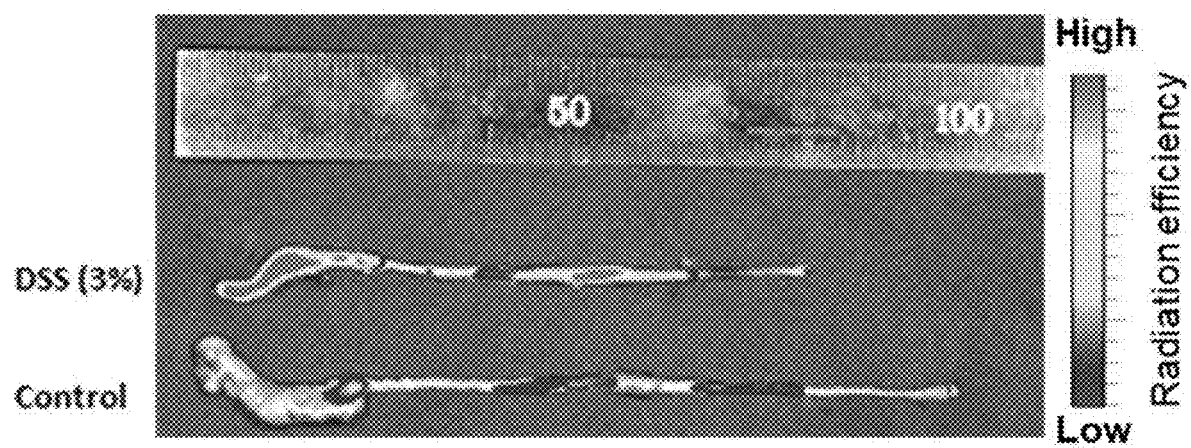
FIG. 6D shows a result of comparing fluorescence from the large intestine of a colitis animal model (DSS) and a control group (normal).

FIG. 6D shows a result of comparing the fluorescence from the large intestine of the colitis animal model (DSS) and the control group (normal). Strong red fluorescence was observed in the large intestine extracted from the colitis animal model.

Figure 6E:
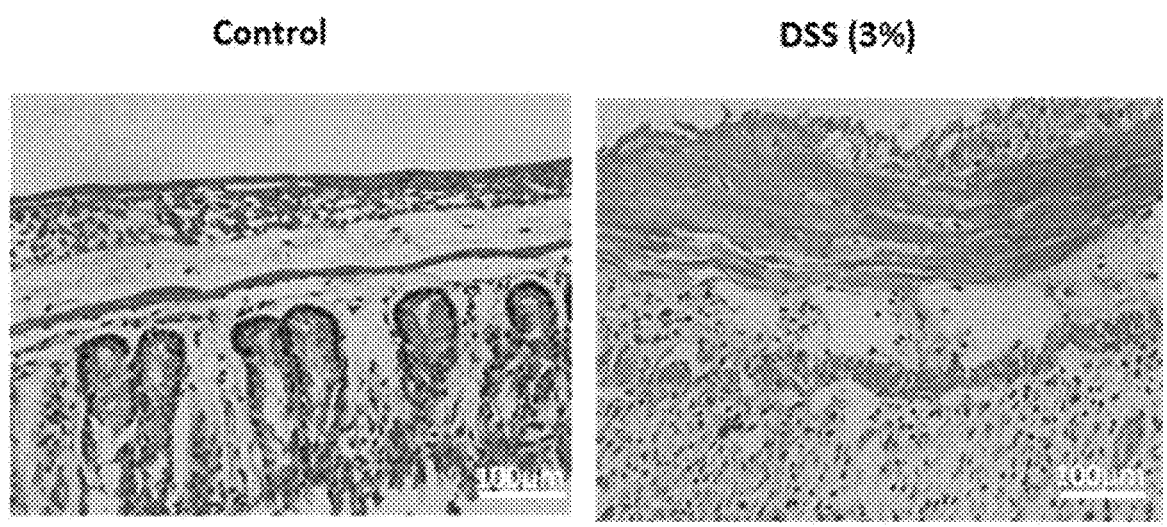
FIG. 6E shows a result of preparing samples of a colitis animal model (DSS) and a control group (normal) and investigating the degree of damage to the large intestine through biopsy and hematoxylin-eosin staining on day 6.

FIG. 6E shows a result of preparing samples of the colitis animal model (DSS) and the control group (normal) and investigating the degree of damage to the large intestine through biopsy and hematoxylin-eosin staining on day 6. It can be seen that the damage to colon cells was induced in the colitis animal model (DSS). This is consistent with the result measured with the probe for measuring the activity of caspase-1 of Example 4.

Figure 6F:
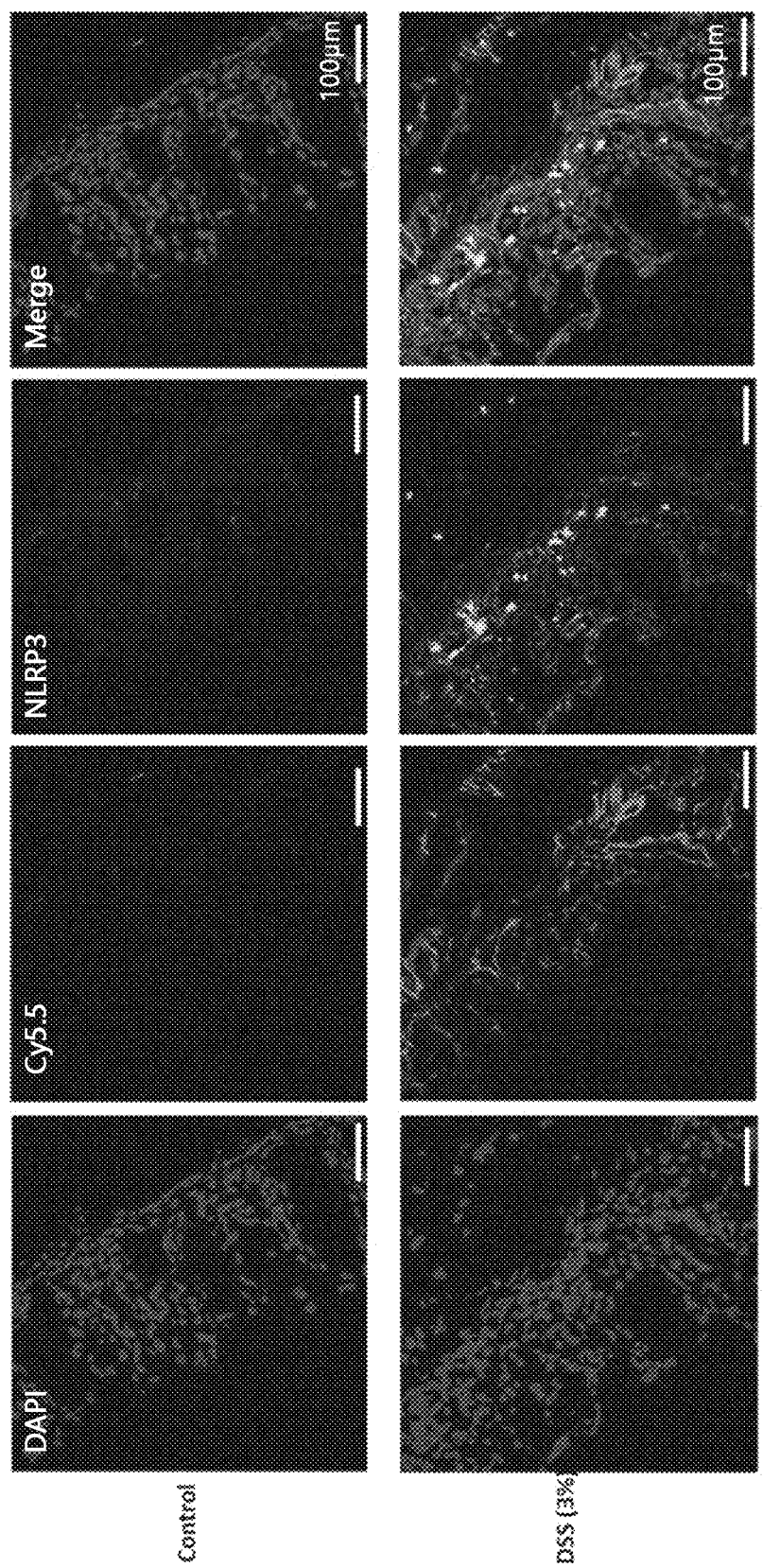
FIG. 6F shows a result of preparing colon cells isolated from a colitis animal model (DSS) and a control group (normal) and imaging the cells with a fluorescence microscope after immunologically staining the inflammasome marker NLRP3 inflammasome. Cy5.5 is shown in red color, and NLRP3 inflammasome is shown in green color.

FIG. 6F shows a result of preparing colon cells isolated from the colitis animal model (DSS) and the control group (normal) and imaging the cells with a fluorescence microscope after immunologically staining the inflammasome marker NLRP3 inflammasome. Cy5.5 is shown in red color, and NLRP3 inflammasome is shown in green color.

It was confirmed that the fluorophore of Cy5.5 was restored by the probe for measuring the activity of caspase-1 of Example 4 only in the colon cells isolated from the colitis animal model.

Test Example 8. Analysis of Alzheimer's Animal Model Using Probe for Measuring Activity of Caspase-1

In order to establish an Alzheimer's animal model, 3- to 6-month-old B6SJL-Tg (APPSwFILon, PSEN1*M146L*L286V)6799Vas/Mmjax) mice acquired from the Jason Laboratory (Bar Harbor, USA) were accustomed for a week and then reared in animal plastic cages, with 4 mice per cage. The cage was controlled with artificial lighting for 12 hours from 7 am to 7 pm, indoor temperature of 18-23° C. and 40-60% humidity. Clean water and feed were given freely. An Alzheimer's animal model was induced through genetic APP mutation. Amyloid beta, which is the cause of dementia, is accumulated from 3 months later and form aggregates 4 months later. The Alzheimer's animal model begins to show behavioral disorder from 5 months and shows general behavioral 6 months later. A control group (pre) was not subjected to the genetic mutation.

In this experiment, 3-month and 4-month Alzheimer's disease (AD) animal models, which do not show the clinical symptoms of Alzheimer's disease, were diagnosed.

Figure 7A:
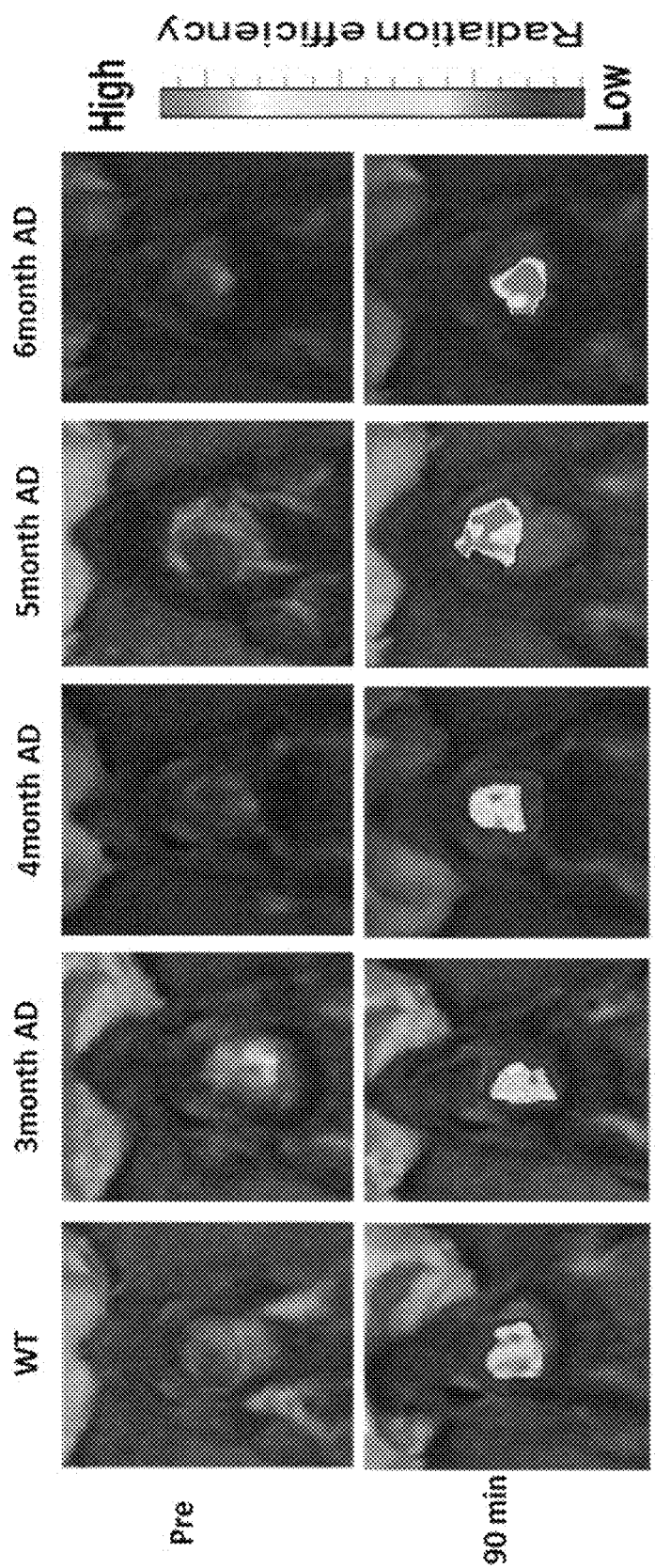
FIG. 7A shows a result of intravenously injecting a probe for measuring the activity of caspase-1 of Example 4 to Alzheimer's animal models of 3-6 months and obtaining fluorescence images 90 minutes later.

FIG. 7A shows a result of intravenously injecting the probe for measuring the activity of caspase-1 of Example 4 to the Alzheimer's animal models of 3-6 months and obtaining fluorescence images 90 minutes later. It can be seen that, with the progress of Alzheimer's disease, amyloid beta aggregates are accumulated and they activate caspase-1 by acting as an inflammation source, which could be observed with the probe for measuring the activity of caspase-1 of Example 4. In addition, it was confirmed that, whereas fluorescence was hardly observed in the control group (pre), the fluorescence could be observed in the Alzheimer's animal model from 3 months, when the clinical symptoms did not occur.

Figure 7B:
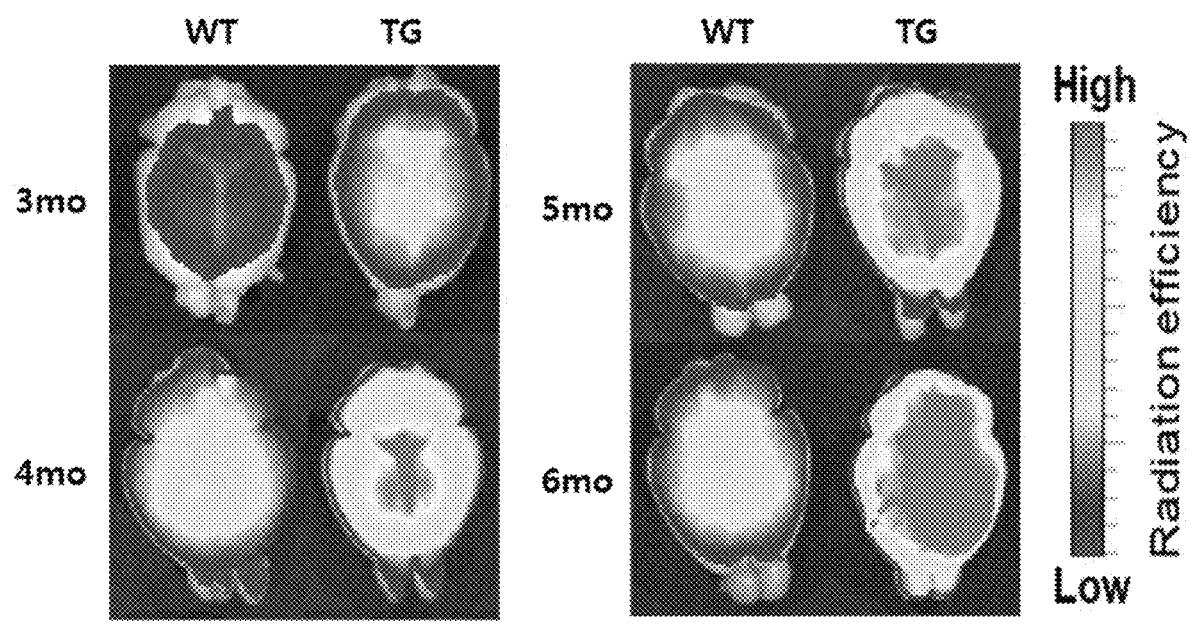
FIG. 7B shows a result of treating Alzheimer's animal models of 3-6 months (3, 4, 5 and 6 months) with a probe for measuring the activity of caspase-1 of Example 4 and measuring fluorescence from the brain.

FIG. 7B shows a result of treating the Alzheimer's animal models of 3-6 months (3, 4, 5 and 6 months) with the probe for measuring the activity of caspase-1 of Example 4 and measuring fluorescence from the brain. It was confirmed that fluorescence was observed in the brain of the Alzheimer's animal model from 4 months and the intensity of fluorescence grew stronger in the Alzheimer's animal models of 5 and 6 months.

Figure 7C:
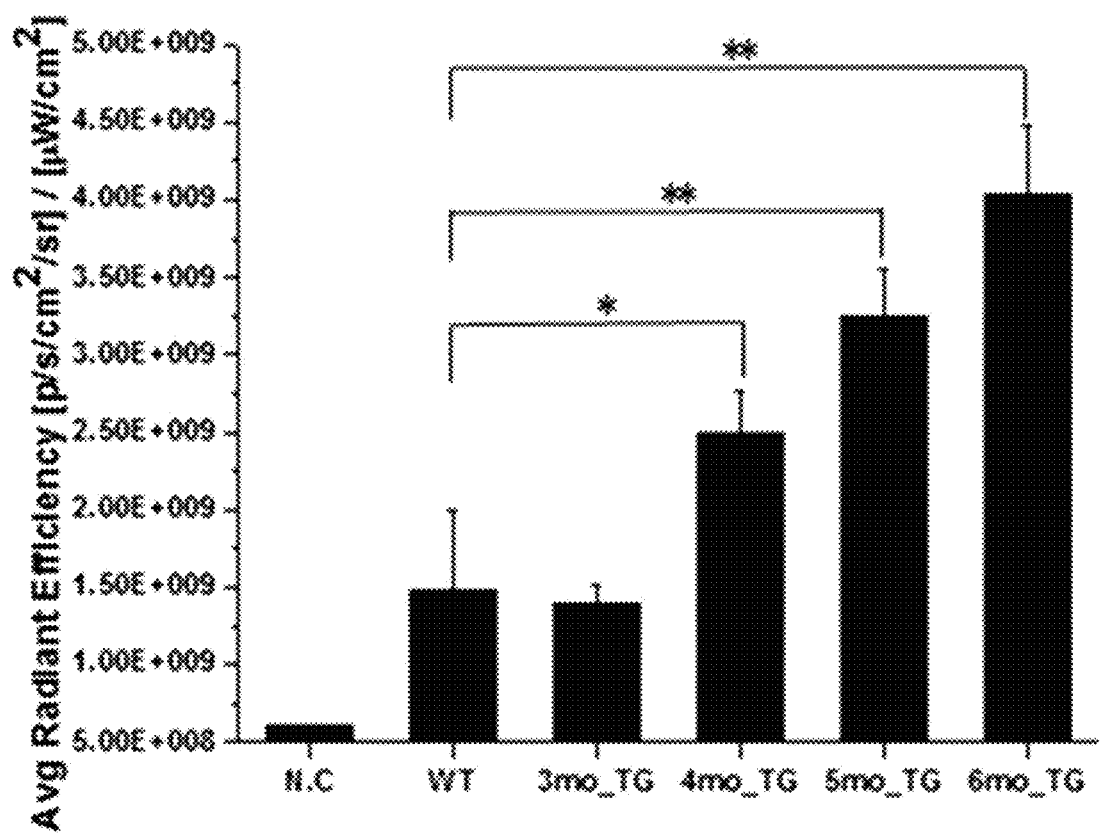
FIG. 7C shows a result of quantifying FIG. 7B.

FIG. 7C shows a result of quantifying FIG. 7B. It was confirmed that significant fluorescence intensity began to be observed starting from the Alzheimer's animal model of 4 months as compared to the control group (WT).

Figure 7D:
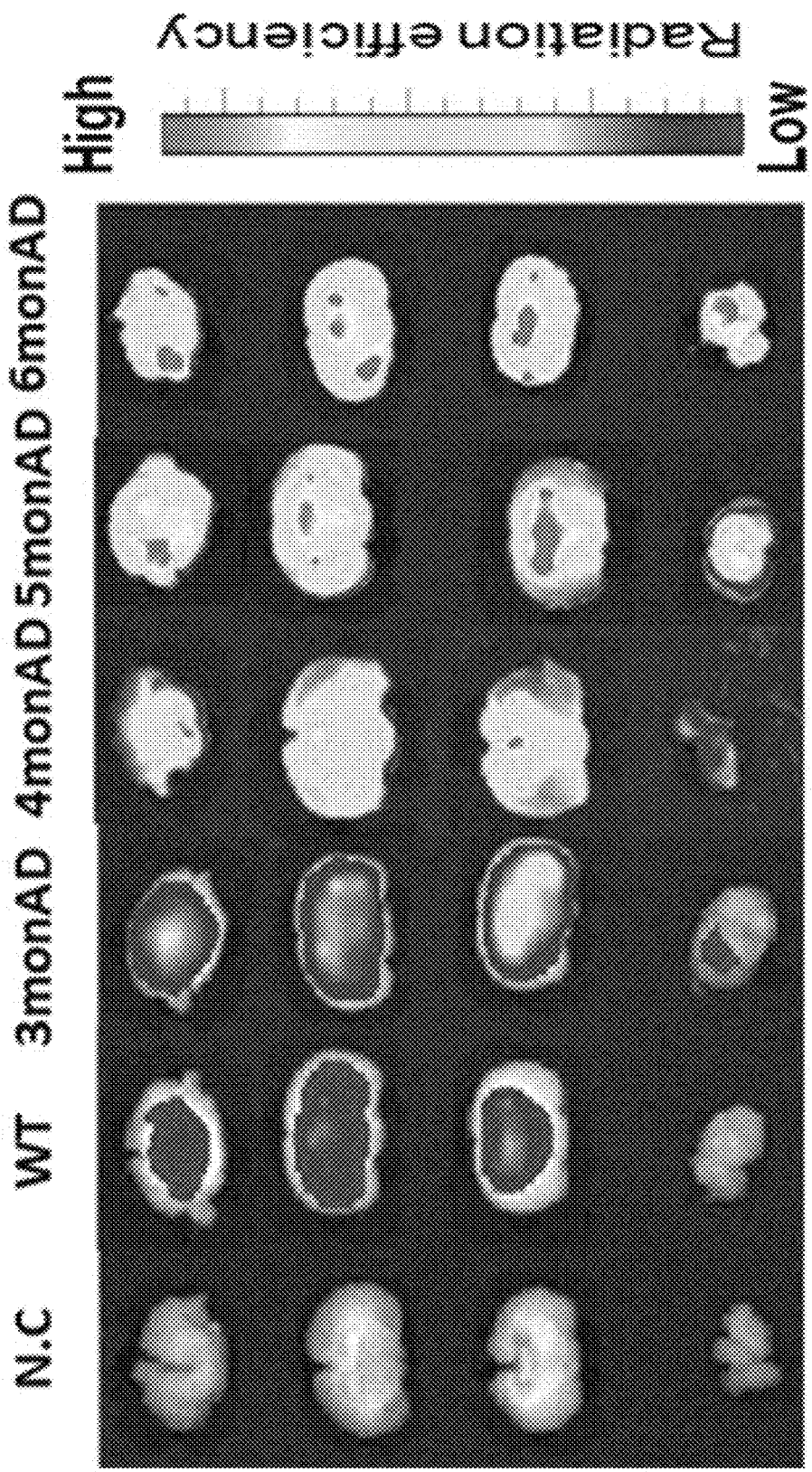
FIG. 7D shows a result of treating Alzheimer's animal models of 3-6 months (3, 4, 5 and 6 months) with a probe for measuring the activity of caspase-1 of Example 4, and quadrisecting and imaging the brain with a fluorescence microscope.

FIG. 7D shows a result of treating the Alzheimer's animal models of 3-6 months (3, 4, 5 and 6 months) with the probe for measuring the activity of caspase-1 of Example 4, and quadrisecting and imaging the brain with a fluorescence microscope. It was confirmed that, when the probe for measuring the activity of caspase-1 prepared in Example 4 was administered to the animal, fluorescence was restored in the brain of the Alzheimer's animal model and the fluorescence was observed clearly in the hippocampal region of the brain, where Alzheimer's disease begins.

Figure 7E:
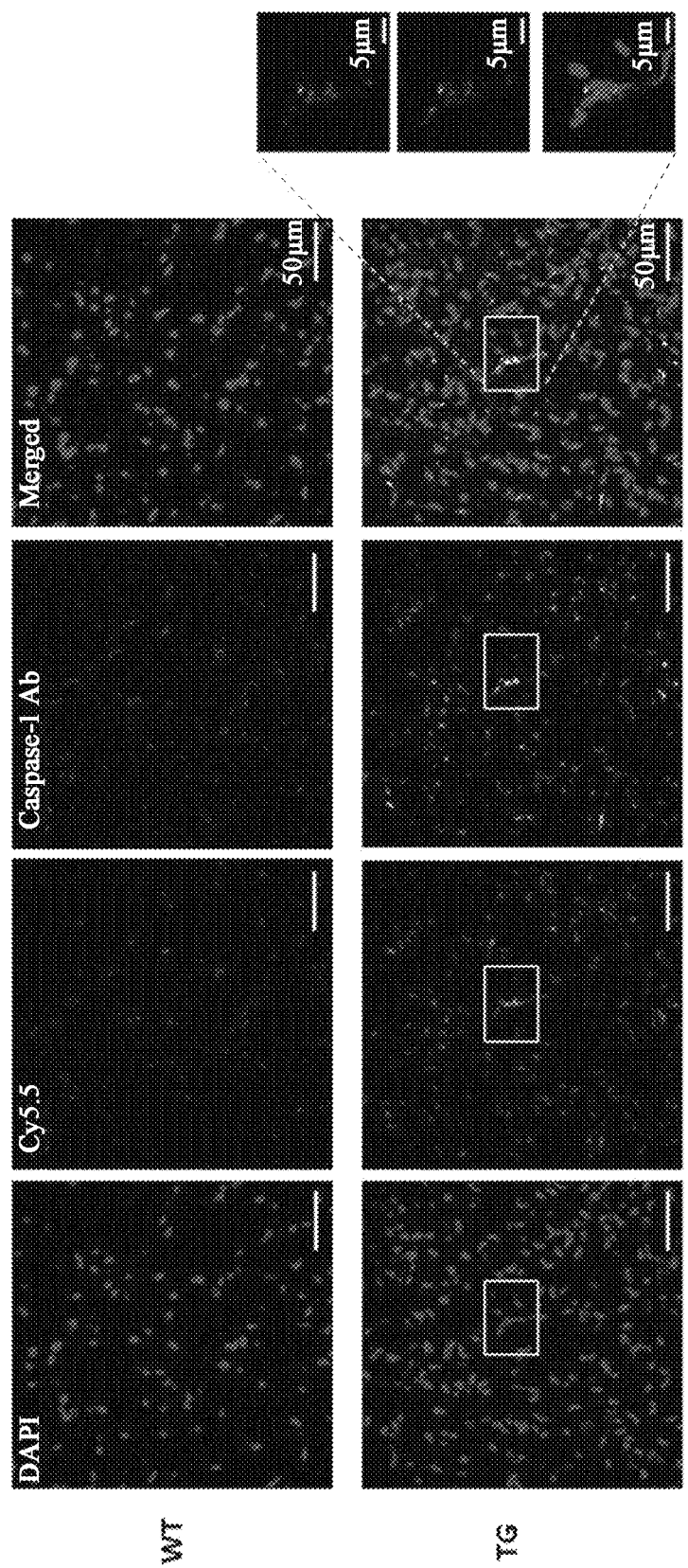
FIG. 7E shows a result of treating an Alzheimer's animal model of 3 months (TG) with a probe for measuring the activity of caspase-1 of Example 4 and imaging the brain tissue 3 hours later with a fluorescence microscope after immunologically staining with the caspase-1 marker caspase-1' Ab.

FIG. 7E shows a result of treating the Alzheimer's animal model of 3 months (TG) with the probe for measuring the activity of caspase-1 of Example 4 and imaging the brain tissue 3 hours later with a fluorescence microscope after immunologically staining with the caspase-1 marker caspase-1' Ab. Caspase-1' Ab denotes treatment with the caspase-1 antibody and is shown in green color. Cy5.5 denotes treatment with the fluorophore (Cy5.5) of the probe for measuring the activity of caspase-1 and is shown in red color.

As seen from FIG. 7E, it was confirmed that the region of fluorescence emission by the probe for measuring the activity of caspase-1 of Example 4 corresponds exactly to the region immunologically stained with the caspase-1 antibody. This suggests that the probe for measuring the activity of caspase-1 of the present disclosure emits fluorescence by reacting specifically with the caspase-1 enzyme.

What is claimed is:

1. A probe for measuring the activity of caspase-1, comprising:
   a polypeptide (a) consisting of the amino acid sequence of SEQ ID NO: 1, wherein the polypeptide (a) is cleaved by the capase-1;
   a fluorophore (b) bound to one end of the polypeptide (a); and
   a quencher (c) bound to the other end of the polypeptide (a),
   wherein the fluorophore (b) is bound to the N-terminal of the polypeptide (a), and the quencher (c) is bound to the ε-amine group of a lysine or arginine amino acid residue of the polypeptide (a),
wherein the fluorophore (b) is any one selected from a group consisting of fluorescein, fluorescein isothiocyanate (FITC), Oregon green, Texas red, Cy2, Cy3, Cy3B, Cy3.5, Cy5, Cy5.5, Cy7, indocarbocyanine, rhodamine, oxacarbocyanine, thiacarbocyanine, merocyanine, pyrodyloxazole, nitrobenzoxadiazole, benzoxadiazole, Nile red, Nile orange, acridine yellow, aumarine, crystal violet and malachite green,
wherein the quencher (c) is any one selected from a group consisting of TAMRA (6-carboxytetramethyl-rhodamine), black hole quencher 1 (BHQ1), black hole quencher 2 (BHQ2), black hole quencher 3 (BHQ3), nonfluorescent quencher (NFQ), DABCYL, Eclipse, deep dark quencher (DDQ), BlackBerry Quencher and Iowa black.

2. The probe for measuring the activity of caspase-1 according to claim 1, wherein the probe emits fluorescence when cleaved by the caspase-1 activated by inflammation.

3. The probe for measuring the activity of caspase-1 according to claim 1, wherein the probe for measuring the activity of caspase-1 is cleaved by the active caspase-1 enzyme expressed in an inflammatory cell, thereby restoring fluorescence.

4. The probe for measuring the activity of caspase-1 according to claim 1, wherein the probe for measuring the activity of caspase-1 further comprises a drug or a nanoparticle, and the drug or the nanoparticle is bound to a carboxyl group at the C-terminal of the polypeptide (a).

5. A composition for qualitatively or quantitatively analyzing the caspase-1 enzyme expressed in a cell or a tissue, which comprises the probe for measuring the activity of caspase-1 according to claim 1 as an active ingredient.

6. A method for imaging a cell or a tissue where an inflammatory response is induced from an individual, which comprises:
 1) administering the probe for measuring the activity of caspase-1 according to claim 1 to the individual; and
 2) obtaining an image with the probe for measuring the activity of caspase-1 from the individual.

* * * * *